US012686704B2

(12) United States Patent
Nadir

(10) Patent No.: US 12,686,704 B2
(45) Date of Patent: Jul. 21, 2026

(54) PROCOAGULANT PEPTIDES AND USE THEREOF

(71) Applicant: RAMBAM MED-TECH LTD., Haifa (IL)

(72) Inventor: Yona Nadir, Zichron Yaakov (IL)

(73) Assignee: RAMBAM MED-TECH LTD., Haifa (IL)

(*) Notice: Subject to any disclaimer, the term of this patent is extended or adjusted under 35 U.S.C. 154(b) by 456 days.

(21) Appl. No.: 18/287,276

(22) PCT Filed: Apr. 18, 2022

(86) PCT No.: PCT/IL2022/050403
§ 371 (c)(1),
(2) Date: Oct. 17, 2023

(87) PCT Pub. No.: WO2022/224249
PCT Pub. Date: Oct. 27, 2022

(65) Prior Publication Data

US 2024/0199703 A1 Jun. 20, 2024

Related U.S. Application Data

(60) Provisional application No. 63/176,311, filed on Apr. 18, 2021.

(51) Int. Cl.

| | |
|---|---|
| ***C07K 14/00*** | (2006.01) |
| ***A61K 38/00*** | (2006.01) |
| ***A61L 15/32*** | (2006.01) |
| ***A61P 7/04*** | (2006.01) |
| ***C07K 4/00*** | (2006.01) |

(52) U.S. Cl.
CPC ............ *C07K 14/001* (2013.01); *A61L 15/32* (2013.01); *A61P 7/04* (2018.01); *C07K 4/00* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 9,321,826 | B2 | 4/2016 | Camire et al. |
| 2013/0157949 | A1 | 6/2013 | Al-Mahmood et al. |
| 2013/0252896 | A1 | 9/2013 | Dockal et al. |
| 2017/0322227 | A1 | 11/2017 | Laurie |
| 2019/0219601 | A1 | 7/2019 | Nadir et al. |

OTHER PUBLICATIONS

Merkler, D.J., C-terminal amidated peptides: production by the in vitro enzymatic amidation of glycine-extended peptides and the importance of the amide to bioactivity. Enzyme Microb Technol. Jun. 1994;16(6):450-6. doi: 10.1016/0141-0229(94)90014-0. PMID: 7764886.

Crispel Y, Ghanem S, Attias J, Kogan I, Brenner B, Nadir Y. Involvement of the heparanase procoagulant domain in bleeding and wound healing. J Thromb Haemost. Jul. 2017;15(7):1463-1472. doi: 10.1111/jth.13707. Epub Jun. 4, 2017. PMID: 28439967.

Morgan CE, Prakash VS, Vercammen JM, Pritts T, Kibbe MR. Development and validation of 4 different rat models of uncontrolled hemorrhage. JAMA Surg. Apr. 2015;150(4):316-24. epub Feb. 18, 2015. doi: 10.1001/jamasurg.2014.1685. PMID: 25693160.

PCT International Search Report for International Application No. PCT/IL2022/050403, mailed Aug. 4, 2022, 3pp.

PCT Written Opinion for International Application No. PCT/IL2022/050403, mailed Aug. 4, 2022, 5pp.

PCT International Preliminary Report on Patentability for International Application No. PCT/IL2022/050403, issued Oct. 24, 2023, 6pp.

Crispel Y. et al.: "Involvement of the heparanase procoagulant domain in bleeding and wound healing", Journal of Thrombosis and Haemostasis, vol. 15, No. 7, Jun. 4, 2017, pp. 1463-1472, XP055977825, GB; ISSN: 1538-7933, DOI: 10.1111/jth.13707; Retrieved from the Internet: URL:https://onlinelibrary.wiley.com/doi/full-xml/10.1111/jth.13707>.

Merkler et al.: "C-Terminal amidated peptides: Production by the in vitro enzymatic amidation of glycine-extended peptides and the importance of the amide to bioactivity", Enzyme and Microbial Technology, Stoneham, MA, US, vol. 16, No. 6, Jun. 1, 1994 (Jun. 1, 1994), pp. 450-456, XP023787769, ISSN: 0141-0229, DOI: 10.1016/0141-0229(94)90014-0.

*Primary Examiner* — Christina Bradley
(74) *Attorney, Agent, or Firm* — The Roy Gross Law Firm, LLC; Roy D. Gross

(57) ABSTRACT

There is provided procoagulant peptides, and use of same, such as in treatment of hemostasis-related diseases or disorders, and/or wound healing.

8 Claims, 14 Drawing Sheets

Specification includes a Sequence Listing.

Control

Peptide 16

Peptide 16AC

PROCOAGULANT PEPTIDES AND USE THEREOF

CROSS-REFERENCE TO RELATED APPLICATIONS

This application is a National Phase of PCT Patent Application No. PCT/IL2022/050403 having International filing date of 18 Apr. 2022, which claims the benefit of priority of U.S. Provisional Patent Application No. 63/176,311, titled "PROCOAGULANT PEPTIDES AND USE THEREOF", filed Apr. 18, 2021, the contents of which are incorporated herein by reference in their entirety.

FIELD OF THE INVENTION

The invention relates generally to the field of, inter alia, procoagulant peptides and their utilization in hemostasis, thrombus, angiogenesis, and wound healing.

BACKGROUND

There are various applications for procoagulants to assist animals and humans with reduced and absent coagulation factors. Disorders such as hemophilia; genetic mutations of various proteins involved in the coagulation cascade; acquired coagulation disorders; treatment of persons in emergency or trauma situations and war zones illustrate some of these applications.

In bleeding disorders and other situations where coagulation is reduced or ceases, hemostasis and angiogenesis must be upregulated in order to remedy these deficiencies. Uncontrolled bleeding is one of the most significant indications of disease and may be localized or generalized. Localized bleeding may be associated with injuries of tissues and organs and may be aggravated with a defective hemostatic regulation system.

Increased levels of hemorrhaging may be as a result of congenital or acquired deficiencies of any of the coagulation factors that form part of the hemostatic regulation system. Treatments to date have centered around whole blood transfusions, platelet transfusions, factor replacement which have shown not to be safe or not to always be effective. A significant number of recipients of chronic factor replacement therapy may generate neutralizing antibodies to replacement factors, leading to further complications.

Thus, there remains a need for new therapeutic agent(s) and approaches for treating bleeding disorders. A single pharmaceutical agent that is safe, convenient and effective in a broad range of bleeding disorders would favorably impact clinical practice.

SUMMARY

The present invention, in some embodiments, provides a procoagulant peptide, and use thereof in promoting hemostasis, thrombus, angiogenesis, wound healing, or any combination thereof.

The present invention, in some embodiments, is based, at least in part, on the findings that modified peptides as disclosed, were shown to be highly effective in inducing coagulation of whole blood (Example 1), reducing massive bleeding, in two in vivo rat models (Example 2) an in hemophilia mice (Example 3), and in a wound healing model in mice (Example 4). Further, exemplified herein is increased efficacy of the peptide of the invention in inducing angiogenesis, endothelial cell proliferation, and endothelial cell migration. In all experiments a significant increase in efficacy was demonstrated with a peptide having 6 to 25 amino acids, e.g., the sequence GSKRRKLRVYLHCT, being modified with an acetyl group, optionally further modified by an amid group.

According to a first aspect, there is provided a peptide of 6 to 25 amino acids comprising SEQ ID NO: 1 (KRRKLR) comprising a C-terminal amid group.

According to another aspect, there is provided a peptide of 6 to 25 amino acids comprising SEQ ID NO: 1 (KRRKLR), or a functional analog thereof, wherein the peptide comprises a C-terminal amid group and an N-terminal acyl group.

According to another aspect, there is provided a pharmaceutical composition comprising the peptide disclosed herein, and a pharmaceutically acceptable carrier.

According to another aspect, there is provided a wound dressing comprising any one of: (a) the peptide disclosed herein; and (b) the pharmaceutical composition disclosed herein.

According to another aspect, there is provided a method for treating a subject in need of wound healing, the method comprising administering to the subject a therapeutically effective amount of a pharmaceutical composition comprising a peptide of 6 to 25 amino acids comprising SEQ ID NO: 1 (KRRKLR), or a functional analog thereof, the peptide comprising: (i) a C-terminal amid group or (ii) a C-terminal amid group and an N-terminal acyl group, thereby treating the subject in need of wound healing.

According to another aspect, there is provided a method for treating a subject in need of induction of coagulation, the method comprising administering to the subject a therapeutically effective amount of a pharmaceutical composition comprising a peptide of 6 to 25 amino acids comprising SEQ ID NO: 1 (KRRKLR) comprising: (i) a C-terminal amid group or (ii) a C-terminal amid group and an N-terminal acyl group, thereby treating the subject in need of induction of coagulation.

In some embodiments, the acyl is acetyl.

In some embodiments, the peptide comprises at least 10 amino acid residues.

In some embodiments, the peptide comprises 12 to 25 amino acids.

In some embodiments, the peptide comprises the amino acid sequence:

```
                                        (SEQ ID NO: 4)
                    GSKRRKLRVYLH.
```

In some embodiments, the peptide comprises SEQ ID NO: 2 (GSKRRKLRVYLHCT).

In some embodiments, the peptide comprises SEQ ID NO: 3 (VQGSKRRKLRVYLH).

In some embodiments, the peptide is a procoagulant peptide.

In some embodiments, the pharmaceutical composition is for use in the treatment of a subject in need of induction of coagulation.

In some embodiments, the subject is afflicted with a wound, hemorrhage, or both.

In some embodiments, the subject is afflicted with a disease or a disorder being selected from the group consisting of: hemostatic disorder, anticoagulation disorder, angiogenesis-related disease, and any combination thereof.

In some embodiments, the hemostatic disorder is an anticoagulation disorder.

In some embodiments, the anticoagulation disorder is hemophilia.

In some embodiments, the administering comprises: subcutaneously administering, intravenously administering, topically administering, or any combination thereof.

In some embodiments, the treating comprises: increasing serum levels of factor Xa, reducing time of clot formation, increasing thrombus strength, reducing volume or weight of lost blood, reducing bleeding time, reducing wound size, increasing the number of blood vessels, and any combination thereof, in the subject.

In some embodiments, the treating comprises increasing the number of: proliferating endothelial cells, migrating endothelial cells, or both.

In some embodiments, the treating comprises increasing expression, abundance, secretion, or any combination thereof, of at least one biomarker coagulation marker being selected form the group consisting of: heparanase, tissue factor (TF), tissue factor pathway inhibitor (TFPI), TFPI-2, and any combination thereof, in the subject.

In some embodiments, the treating comprises increasing phosphorylation rate of p38 mitogen-activated protein kinase (p38), abundance of phosphorylated p38, or both, in the subject.

In some embodiments, the increasing is in a cell of the subject.

In some embodiments, the cell is an endothelial cell.

In some embodiments, the method further comprises a step of determining in a sample obtained or derived from the subject: serum levels of factor Xa, time of clot formation, thrombus strength, volume or weight of lost blood, bleeding time, wound size, number of blood vessels, number of proliferating endothelial cells, number of migrating endothelial cells, expression, abundance, secretion, or any combination thereof, of at least one coagulation biomarker or marker being selected form the group consisting of: heparanase, tissue factor (TF), tissue factor pathway inhibitor (TFPI), TFPI-2, and any combination thereof, phosphorylation rate of p38 mitogen-activated protein kinase (p38), abundance of phosphorylated p38, or any combination thereof.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

Some embodiments of the invention are herein described, by way of example only, with reference to the accompanying figures.

With specific reference now to the figures in detail, it is stressed that the particulars shown are by way of example and for purposes of illustrative discussion of embodiments of the invention. In this regard, the description together with the drawings makes apparent to those skilled in the art, how embodiments of the invention may be practiced. Dimensions of components and features shown in the figures are generally chosen for convenience and clarity of presentation and are not necessarily shown to scale. The figures are listed below.

DETAILED DESCRIPTION OF THE INVENTION

Figure 1A:
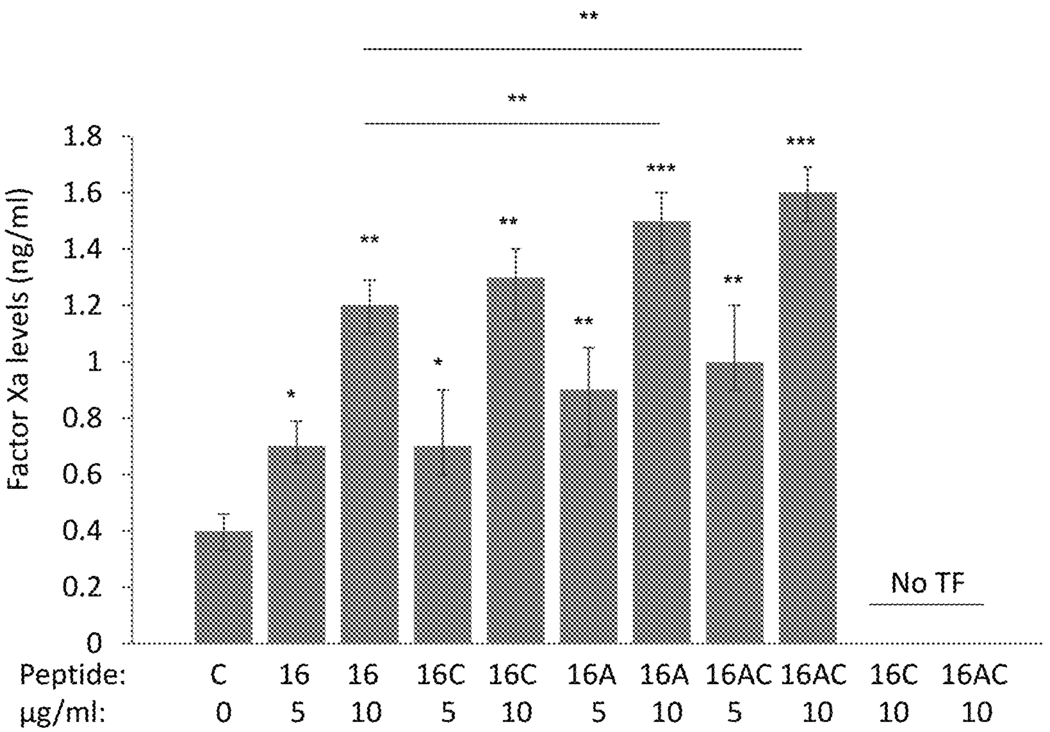
FIGS. 1A-1C include vertical bar graphs and thromboelastography (TEG) curves, showing that peptide 16 and peptide 16AC increase coagulation. Peptide 16 and 16AC were studied in an assay of purified proteins that included lipidated TF (4 nM), factor VIIa (40 nM), factor X (1.4 μM) and assay buffer. Factor X activated form (Xa) level was studied using a chromogenic substrate (1 mM). The peptides at a dose of 5 μg/ml and 10 μg/ml (3.75 μM and 7.5 μM, respectively) significantly increased activation of factor X compared to control (1A), thus increasing activation of the coagulation system. Bovine factor Xa diluted in the assay buffer was used to generate a standard curve. Without addition of TF (two right columns), no factor Xa was generated. These results represent a mean of triplicate and range. *$p<0.01$, $p<0.001$, *$p<0.0001$. (1B) A citrated pooled normal human blood sample (n=3) was left for 4 hours at room temperature in order to expose TF in bloods cells. Following this period, the peptides 16 and 16AC were added (5 μg/ml) along with calcium. The peptides significantly reduced the time to clot formation (R) and increased thrombus strength, as indicated by a greater maximal amplitude (MA). Representative TEG curves are shown. (1C) The study presented in FIG. 1B was repeated 3 times with different pooled plasma. These results represent a mean of triplicate and range. *$p<0.01$, $p<0.001$. The modified peptide 16AC demonstrated significantly better effect on clot formation compared to peptide 16. Peptide 16 (non-modified); peptide 16 comprising a C-terminal amid group (16A); peptide 16 comprising an N-terminal acetyl group (16C); and peptide 16 comprising a C-terminal amid group and an N-terminal acetyl group (16AC). In 1**B: for control—SP min=11.2; R min=12.8; K min=3.8, Angle deg=52.0; and MA mm=47.9, for Peptide 16—SP min=5.2; R min=6.4; K min=2.8, Angle deg=63.3; and MA mm=50.4, and for Peptide 16AC—SP min=4.7; R min=5.6; K min=2.5, Angle deg=63.1; and MA mm=53.8.

The following embodiments and aspects thereof are described and illustrated in conjunction with systems, tools and methods which are meant to be exemplary and illustrative, not limiting in scope.

According to some embodiments, there is provided a peptide of 6 to 25 amino acids comprising SEQ ID NO: 1 (KRRKLR) comprising a C-terminal amid group, or a functional analog thereof.

According to some embodiments, there is provided a peptide of 6 to 25 amino acids comprising SEQ ID NO: 1 (KRRKLR), a C-terminal amid group and an N-terminal acetyl group, or a functional analog thereof.

According to some embodiments, there is provided a peptide of 12 to 25 amino acids comprising the amino acid sequence: GSKRRKLRVYLH (SEQ ID NO: 4) comprising a C-terminal amid group, or a functional analog thereof.

According to some embodiments, there is provided a peptide of 12 to 25 amino acids comprising the amino acid sequence: GSKRRKLRVYLH (SEQ ID NO: 4) comprising a C-terminal amid group and an N-terminal acyl group, or a functional analog thereof.

According to some embodiments, there is provided a peptide of 12 to 25 amino acids comprising the amino acid sequence: GSKRRKLRVYLH (SEQ ID NO: 4), and further comprising a C-terminal amid group and an N-terminal acyl group, or a functional analog thereof.

In some embodiments, acyl comprises acetyl.

In some embodiments, the peptide comprises at least 10, at least 11, at least 12, at least 13, at least 14, at least 15, at least 16, at least 17, at least 18, at least 19, at least 20, at least 21, at least 22, at least 23, at least 24 amino acid residues, or any value and range therebetween. Each possibility represents a separate embodiment of the invention.

In some embodiments, the peptide comprises SEQ ID NO: 2 (GSKRRKLRVYLHCT).

In some embodiments, the peptide comprises SEQ ID NO: 3 (VQGSKRRKLRVYLH).

In some embodiments, the peptide comprises or consists of (SEQ ID NO: 6)
GSKRRKLRVYLHCT-amid.

In some embodiments, the peptide comprises or consists of acetyl- (SEQ ID NO: 7)
GSKRRKLRVYLHCT-amid.

In some embodiments, the peptide comprises or consists of (SEQ ID NO: 8)
VQGSKRRKLRVYLH-amid.

In some embodiments, the peptide comprises or consists of acetyl- (SEQ ID NO: 9)
VQGSKRRKLRVYLH-amid.

In some embodiments, the modified peptide of the invention is a procoagulant peptide or characterized by procoagulation or procoagulating activity.

As used herein, the terms "procoagulant", "procoagulation", and "procoagulating" are interchangeable, and refer to promoting blood clotting, e.g., the changes of blood from liquid to a gel, culminating with the formation of a blood clot.

In some embodiments, the modified peptide comprises at least one post-translational modification. In some embodiments, the peptide comprises at least one post-translational modification at the N-, or both the N- and C-termini of the peptide, as long as the modification enhances or does not hamper the peptide's stability, activity, or both.

In some embodiments, a functional analog comprises any peptide of 6 to 25 amino acids comprising any one of SEQ ID Nos: 1-4 or having at least 70%, 80%, 90%, 95%, or 99% sequence homology thereto, comprising N-terminal acetyl group, or N-terminal acetyl group and a C-terminal amid group, as long its procoagulant effect or activity, as disclosed herein, is at least 70%, 80%, 90%, 95%, or 99% of the procoagulant effect of the modified peptide of the invention.

The present invention also contemplates analogs of the peptides disclosed herein, as long as the analogs have procoagulant, prothrombic, improved wound healing or angiogenic effects. The term "analog" includes any peptide having an amino acid sequence substantially identical to one of the sequences specifically shown herein, in which one or more residues have been conservatively substituted with a functionally similar residue and which displays the abilities as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. Each possibility represents a separate embodiment of the present invention.

Conservative substitution of amino acids, as known to those skilled in the art, are within the scope of the present invention. Conservative amino acid substitutions include replacement of one amino acid with another having the same type of functional group or side chain e.g., aliphatic, aromatic, positively charged, negatively charged. One of skill will recognize that individual substitutions, deletions or additions to peptide, polypeptide, or protein sequence which alters, adds, or deletes a single amino acid or a small percentage of amino acids in the encoded sequence is a "conservatively modified variant", where the alteration results in the substitution of an amino acid with a chemically similar amino acid. Conservative substitution tables providing functionally similar amino acids are well known in the art.

The following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W) (see, e.g., Creighton, Proteins, 1984).

The term "conservative substitution" also includes the use of a chemically derivatized residue in place of a non-derivatized residue, provided that such peptide displays the requisite function of enhancing or, at least, does not hamper the peptide's stability or its procoagulant effect as specified herein.

In one embodiment, the present invention provides a modified peptide of up to 25 amino acids comprising SEQ ID NO: 1 (KRRKLR), or a functional analog thereof, the modified peptide comprises a C-terminal amid group. In one embodiment, the modified peptide further comprises an N-terminal acetyl group.

In another embodiment, the modified peptide comprises the amino acid sequence as set forth in SEQ ID NO: 2 (GSKRRKLRVYLHCT), or a functional analog thereof. In another embodiment, the modified peptide comprises the amino acid sequence as set forth in SEQ ID NO: 2. In another embodiment, the modified peptide consisting of the amino acid sequence as set forth in SEQ ID NO: 2.

In another embodiment, the present modified peptide comprises the amino acid sequence as set forth in SEQ ID NO 3: (VQGSKRRKLRVYLH), or a functional analog thereof. In another embodiment, the modified peptide comprises the amino acid sequence as set forth in SEQ ID NO: 3. In another embodiment, the modified peptide consisting of the amino acid sequence as set forth in SEQ ID NO: 3.

Without limiting the invention to any theory or mechanism of action, the findings presented herein indicate that the positively charged amino acids located in SEQ ID NO: 1, as well as the addition of a further positive charge to the peptide by the amide group account for the increased procoagulant and pro-hemostatic activity as well as wound healing effects.

As exemplified herein below, C-terminal amidation of the peptide of the invention improves the peptide's positive charge, thereby improving its efficacy as a procoagulant and wound healing protagonist. The combined effect of adding a C-terminus amid group and an N-terminus acetyl group mimic the termini of proteins in the body, giving the modified peptide its improved characteristics and effect.

Composition

According to some embodiments, there is provided a composition comprising the peptide of the invention, and an acceptable carrier.

In some embodiments, the carrier comprises or consists of a pharmaceutically acceptable carrier.

In some embodiments, the composition is a pharmaceutical composition.

In some embodiments, the composition is formulated for subcutaneous administration, intravenous administration, topical administration, or any combination thereof.

In some embodiments, the pharmaceutical composition is for use in prevention or treatment or of a subject in need of induction of coagulation.

In one embodiment, the present invention provides a composition comprising the peptide of the invention and a carrier. In some embodiments, the pharmaceutical composition comprises a therapeutically effective amount of the peptide. In some embodiments, the pharmaceutical composition further comprises other therapeutic ingredient(s) and one or more pharmaceutically acceptable carriers.

In one embodiment, the present invention provides a pharmaceutical composition comprising a therapeutically effective amount of the peptide as described herein and a pharmaceutically acceptable carrier.

In another embodiment, the present invention provides the pharmaceutical composition as detailed herein for use in promoting hemostasis in a subject in need thereof.

In another embodiment, the present invention provides the pharmaceutical composition, as detailed above, for use in promoting wound healing in a subject in need thereof.

The present invention also contemplates pharmaceutical compositions for human medical and veterinary use, which comprise at least one peptide of this invention.

The pharmaceutical compositions of the invention can be formulated in the form of a pharmaceutically acceptable salt of the peptide of the invention or analogs thereof. "Pharmaceutically acceptable salts" include those salts formed with free amino groups such as salts derived from non-toxic inorganic or organic acids such as hydrochloric, phosphoric, acetic, oxalic, tartaric acids, and the like, and those salts formed with free carboxyl groups such as salts derived from non-toxic inorganic or organic bases such as sodium, potassium, ammonium, calcium, ferric hydroxides, isopropylamine, triethylamine, 2-ethylamino ethanol, histidine, procaine, and the like. In one embodiment, pharmaceutical compositions of the present invention are manufactured by processes well known in the art, e.g., by means of conventional mixing, dissolving, granulating, dragee-making, levigating, emulsifying, encapsulating, entrapping or lyophilizing processes.

The term "pharmaceutically acceptable" means suitable for administration to a subject, e.g., a human or animal. For example, the term "pharmaceutically acceptable" can mean approved by a regulatory agency of the Federal or a state government or listed in the U. S. Pharmacopeia or other generally recognized pharmacopeia for use in animals, and more particularly in humans.

The term "carrier" refers to a diluent, adjuvant, excipient, or vehicle with which the therapeutic compound is administered. Such pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerin, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; and agents for the adjustment of tonicity such as sodium chloride or dextrose are also envisioned. The carrier may constitute, in total, from about 0.1% to about 99.99999% by weight of the pharmaceutical compositions presented herein.

An embodiment of the invention relates to a peptide, presented in unit dosage form and, is prepared by any of the methods well known in the art of pharmacy and pharmacology. In an embodiment of the invention, the unit dosage form is in the form of a tablet, capsule, lozenge, wafer, patch, ampoule, vial or pre-filled syringe. In addition, in vitro assays may optionally be employed to help identify optimal dosage ranges. The precise dose to be employed in the formulation will also depend on the route of administration, and the nature of the disease or disorder, and should be decided according to the judgment of the practitioner and each patient's circumstances. Effective doses can be extrapolated from dose-response curves derived from in-vitro or in-vivo animal model test bioassays or systems.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes.

The compositions may comprise preservatives, such as benzalkonium chloride and thimerosal and the like; chelating agents, such as EDTA sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed. The compositions may also comprise local anesthetics or other actives.

In addition, the compositions may further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmellose sodium, crospovidone, guar gum, sodium starch glycolate), buffers (e.g., Tris-HCI., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hydroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

In one embodiment, compositions of the present invention are presented in a pack or dispenser device, such as an FDA approved kit, which contains one or more unit dosage forms containing the active ingredient. In one embodiment, the pack or dispenser device is accompanied by instructions for administration.

In some embodiments, the composition is in the form of, but not limited to, a liquid, gel, solid or biofumigant. In some embodiments, the composition comprises a surfactant to be used for the purpose of emulsification, dispersion, wetting, spreading, integration, disintegration control, stabilization of active ingredients, and improvement of fluidity or rust inhibition.

Suitable routes of administration include, but are not limited to, oral (e.g., sublingual, buccal), parenteral (e.g., intravenous, subcutaneous, intramuscular), intranasal, buccal, topical, aerosol, transdermal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections. In certain embodiments, the composition as described herein is administered in a systemic manner. In certain other embodiments, the composition as described herein is administered in a local rather than a systemic manner.

Pharmaceutical compositions of the invention are formulated in a conventional manner, using one or more pharmaceutically acceptable inactive ingredients that facilitate processing of the active compounds into preparations that are used pharmaceutically. A formulation depends upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In another embodiment, a pharmaceutical composition comprises a mixture of a peptide of the invention or a plurality thereof. and at least one additional active ingredient. In another embodiment, a pharmaceutical composition comprises inactive ingredients, such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition, in some embodiments, facilitates administration of the compound to a mammal.

In some embodiments, the pharmaceutical composition comprises a plurality of molecules of the peptide disclosed herein. In some embodiments, the pharmaceutical composition comprises a plurality of types of the peptides disclosed herein.

In another embodiment, a pharmaceutical composition comprises a peptide of the invention, and/or a pharmaceutically acceptable salt thereof, as an active ingredient in free-acid or free-base form, or in a pharmaceutically acceptable salt form. In another embodiment, the pharmaceutical compositions described herein include the use of N-oxides (if appropriate), crystalline forms, amorphous phases, as well as active metabolites of these compounds having the same type of activity.

In another embodiment, pharmaceutical compositions described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, enteric coated formulations, pulsatile release formulations, multiparticulate formulations, and mixed immediate and controlled release formulations.

In another embodiment, a compound of the invention, or a pharmaceutically acceptable salt thereof, is administered topically. In such embodiments, a compound of the invention, or a pharmaceutically acceptable salt thereof, is formulated into a variety of topically administrable compositions, such as solutions, suspensions, lotions, gels, pastes, shampoos, scrubs, rubs, smears, medicated sticks, medicated bandages, balms, creams or ointments. In another embodiment, a compound of the invention, or a pharmaceutically acceptable salt thereof, is administered topically to the skin of mammal. In another embodiment, a compound of the invention is prepared as a transdermal dosage form.

In another embodiment, the compound of the invention, or a pharmaceutically acceptable salt thereof, is administered systemically. In another embodiment, the compound of the invention, or a pharmaceutically acceptable salt thereof, is administered orally. All formulations for oral administration are in dosages suitable for such administration. In another embodiment, the solid dosage forms disclosed herein are in the form of a tablet, a pill, a powder, a capsule, solid dispersion, solid solution, bioerodible dosage form, controlled release formulations, pulsatile release dosage forms, multiparticulate dosage forms, beads, pellets, granules. In other embodiments, the pharmaceutical formulation is in the form of a powder. In another embodiment, the pharmaceutical formulation is in the form of a tablet. In another embodiment, the pharmaceutical formulation is in the form of a suspension tablet, a fast-melt tablet, a bite-disintegration tablet, a rapid-disintegration tablet, an effervescent tablet, or a caplet. In another embodiment, pharmaceutical formulation is in the form of a capsule.

In another embodiment, the pharmaceutical solid oral dosage forms are formulated to provide a controlled release of the active compound. Controlled release profiles include, for example, sustained release, prolonged release, pulsatile release, and delayed release profiles.

In another embodiment, liquid formulation dosage forms for oral administration are in the form of aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002).

In another embodiment, for buccal or sublingual administration, the compositions optionally take the form of tablets, lozenges, or gels formulated in a conventional manner.

In another embodiment, a compound of the invention, or a pharmaceutically acceptable salt thereof, is formulated into a pharmaceutical composition suitable for intramuscular, subcutaneous, or intravenous injection. Parenteral injections involve either bolus injection and/or continuous infusion.

In another embodiment, a compound of the invention, or a pharmaceutically acceptable salt thereof, is administered intravenously. In another embodiment, a compound of the invention, or a pharmaceutically acceptable salt thereof, is administered subcutaneously.

In another embodiment, there is provided use of a peptide of the invention, or a pharmaceutically acceptable salt thereof, in the manufacture of a medicament or a product for prevention or treatment of a disease, disorder or conditions, as disclosed herein. In some embodiments, the prevention or treatment of a disease, disorder or conditions, as disclosed herein, requires or involves procoagulation, wound healing, angiogenic effects, or any combination thereof.

The dosage of the inventive compositions or extract may vary depending on, for example, the body weight, age, sex, health condition, diet, time of administration, method of administration, excretion rate and disease severity for a certain patient.

In another embodiment, the composition described herein is prepared as a prodrug. A "prodrug" refers to an agent that is converted into the parent drug in vivo. In another embodiment, the design of a prodrug increases the effective water solubility. An example, without limitation, of a prodrug is a compound, which is administered as an ester (the "prodrug") but then is metabolically hydrolyzed to provide the active entity. In certain embodiments, upon in vivo administration, a prodrug is chemically converted to the biologically, pharmaceutically or therapeutically active form of the composition.

In another embodiment, the composition is formulated in a pharmaceutically acceptable composition which refers to a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

In another embodiment, doses employed for adult human treatment are typically in the range of 0.01 mg-5,000 mg per day. In another embodiment, doses employed for adult human treatment are from about 1 mg to about 1,000 mg per day. In one embodiment, the desired dose is conveniently presented in a single dose or in divided doses administered simultaneously or at appropriate intervals, for example as two, three, four or more sub-doses per day. In one embodiment, the daily dosages appropriate for the compound of the invention, or a pharmaceutically acceptable salt thereof, described herein are from about 0.01 to about 50 mg/kg per body weight.

According to some embodiments, there is provided a wound dressing comprising the peptide disclosed herein. According to some embodiments, there is provided a wound dressing comprising the composition or the pharmaceutical composition disclosed herein.

Methods of Use

According to some embodiments, there is provided a method for preventing or treating a subject in need of induction of coagulation.

According to some embodiments, there is provided a method for preventing or treating bleeding or hemorrhage in a subject in need thereof.

According to some embodiments, there is provided a method for inducing wound healing in a subject in need thereof.

According to some embodiments, there is provided a method for preventing or treating a subject afflicted with an anticoagulation-related disease.

According to some embodiments, there is provided a method for preventing or treating a subject afflicted with hemostasis-related disease.

According to some embodiments, there is provided a method for inducing angiogenesis in a subject in need thereof.

In some embodiments, inducing angiogenesis comprises inducing: endothelial cell proliferation, endothelial cell migration, or both, in the subject.

In some embodiments, an anticoagulation-related disease, a hemostasis-related disease, or both, are characterized by hypocoagulation, excessive bleeding, reduced clotting, or any combination thereof.

In some embodiments, hypocoagulation, excessive bleeding, reduced clotting, or any combination thereof, is compared to a normal subject.

In some embodiments, the method comprising administering to the subject a therapeutically effective amount of a pharmaceutical composition comprising a peptide as disclosed herein.

In some embodiments, the subject is afflicted with a wound, hemorrhage, or both.

In some embodiments, the subject is afflicted with trauma.

In some embodiments, the subject is afflicted with a disease or a disorder being selected from: hemostatic disorder, anticoagulation disorder, angiogenesis-related disease, or any combination thereof.

In some embodiments, a hemostatic disorder comprises an anticoagulation disorder.

In some embodiments, an anticoagulation disorder comprises hemophilia.

In some embodiments, the subject is afflicted with hemophilia or is a hemophilic subject.

In some embodiments, administering comprises: subcutaneously administering, intravenously administering, topically administering, or any combination thereof.

In some embodiments, administering comprises subcutaneously administering.

In some embodiments, administering comprises intravenously administering.

In some embodiments, administering comprises topically administering.

In some embodiments, treating comprises: increasing serum levels of factor Xa, reducing time of clot formation, increasing thrombus strength, reducing volume or weight of lost blood, reducing bleeding time, reducing wound size, increasing the number of blood vessels, or any combination thereof, in the subject.

Methods for determining serum levels of factor Xa, time of clot formation, thrombus strength, volume or weight of lost blood, bleeding time, wound size, number of blood vessels, are common and would be apparent to one of ordinary skill in the hematology art. Non-limiting examples of such methods are exemplified herein.

In some embodiments, the treating comprises increasing the number of: proliferating endothelial cells, migrating endothelial cells, or both.

Methods for determining endothelial cells proliferation and/or migration, are common and would be apparent to one of ordinary skill in the art. Non-limiting example for such methods include, but are not limited to FACS analysis, immunohistochemistry using specific proliferation markers, e.g., Ki67, scratch assay, some of which are exemplified herein below.

In some embodiments, the treating comprises increasing expression, abundance, secretion, or any combination thereof, of at least one coagulation marker or biomarker being selected from: heparanase, tissue factor (TF), tissue factor pathway inhibitor (TFPI), TFPI-2, and any combination thereof, in the subject.

Methods for determining expression, abundance, secretion, or any combination thereof, of coagulation marker(s) or biomarker(s) are common and would be apparent to one of ordinary skill in the art. Non-limiting example for such methods include, but are not limited to PCR, real-time RT-PCR, western blot, immunoblot, such as targeting phosphorylated proteins, some of which are exemplified herein below.

In some embodiments, treating comprises increasing phosphorylation rate of p38 mitogen-activated protein kinase (p38), abundance of phosphorylated p38, or both, in the subject.

In some embodiments, increasing is in a cell of a subject.

In some embodiments, a cell comprises an endothelial cell.

In some embodiments, the method further comprises a step of determining in a sample obtained or derived from a subject: serum levels of factor Xa, time of clot formation, thrombus strength, volume or weight of lost blood, bleeding time, wound size, number of blood vessels, number of proliferating endothelial cells, number of migrating endothelial cells, expression, abundance, secretion, or any combination thereof, of at least one biomarker coagulation marker being selected form the group consisting of: heparanase, tissue factor (TF), tissue factor pathway inhibitor (TFPI), TFPI-2, or any combination thereof, phosphorylation rate of p38 mitogen-activated protein kinase (p38), abundance of phosphorylated p38, or any combination thereof, in the subject.

In some embodiments, increasing comprises at least 5%, 25%, 50%, 75%, 100%, 250%, 500%, 750%, or 1,000% increase, or any value and range therebetween. Each possibility represents a separate embodiment of the invention.

In some embodiments, increasing comprises 5-100%, 25-250%, 50-450%, 75-650%, 100-900%, or 250-1,250% increase. Each possibility represents a separate embodiment of the invention.

In some embodiments, reducing comprises at least 5%, 20%, 40%, 50%, 60%, 70%, 80%, 90%, 95%, 99%, or 100% reducing, or any value and range therebetween. Each possibility represents a separate embodiment of the invention.

In some embodiments, reducing comprises 5-10%, 5-40%, 20-50%, 45-80%, 10-90%, or 25-100% reducing. Each possibility represents a separate embodiment of the invention.

According to some embodiments, there is provided a method for inducing proliferation, migration, or both, of an endothelial cell.

In some embodiments, the method comprising contacting the cell with an effective amount of a composition comprising a peptide as disclosed herein.

In some embodiments, the cell is a cell of a subject. In some embodiments, the cell is obtained or derived from a subject.

In some embodiments, the inducing is in vivo, ex vivo, in vitro, or any combination thereof.

In some embodiments, the subject is a mammal subject. In some embodiments, the subject is a human subject.

The terms "reducing" or "reduce" and "inhibiting" or "inhibit" are interchangeable.

In another aspect, the present invention provides a method for promoting hemostasis in a subject in need thereof, the method comprising administering to the subject a therapeutically effective amount of the pharmaceutical composition disclosed herein.

In some embodiments, the invention provides methods for inducing hemostasis in a subject presenting insufficient hemostatic function, such as a subject having, or at risk of developing a disorder associated with hypocoagulation.

As used herein, the term "hypocoagulation." refers to a decreased ability or inability to form blood clots. Such disorders include hemorrhagic disorders, hemophilia, hemophilia A or and disorders resulting from a deficiency in clotting factors or platelet ligands, a deficiency in von Willebrand's factor resulting in von Willebrand disease. The induction of a procoagulant state would prevent or stop spontaneous bleeding and would also be beneficial preceding surgical intervention in a patient, or to promote wound healing.

Hemostasis, as used herein, means the stoppage of bleeding or hemorrhage; or the stoppage of blood flow through a blood vessel or body part.

As used herein, the term "hemostatic disease or disorder" encompasses a genetically inherited or acquired condition characterized by a tendency to hemorrhage, either spontaneously, as a result of trauma, surgery, labor, due to an impaired ability or inability to form a fibrin clot, or as a result of receiving antithrombotic agents.

As used herein, the term "anticoagulation disease or disorder" encompasses any disease or disorder characterized by disruption in a subject's ability to control blood clotting. Such anticoagulation diseases or disorders, include hypocoagulation, e.g., too little clotting, thus include increased risk of bleeding and/or hemorrhage, as well as hypercoagulation, e.g., too much clotting, thus include increased risk of blood clots formation or thrombosis.

In some embodiments, anticoagulation disease or disorder is or comprises hypocoagulation.

As used herein, the term "angiogenesis-related disease" encompasses any disease or disorder involving impaired, reduced, insufficient, or inhibited angiogenesis.

In some embodiments, angiogenesis-related disease comprises or is characterized by reduced number of formed blood vessel, such as in a tissue, including an injured tissue, a post injury tissue, including a scared tissue.

In some embodiments, angiogenesis-related disease comprises or is characterized by reduced endothelial cell proliferation, migration, or both, such as in a tissue, including an injured tissue, a post injury tissue, including a scared tissue.

In one embodiment, the present invention provides a method for promoting wound healing in a subject in need thereof, the method comprising administering the subject with a therapeutically effective amount of the pharmaceutical composition described herein. The administering of the pharmaceutical composition, as described in this embodiment, may be employed using a wound dressing. In another embodiment thereof, the wound dressing may be made of several layers. In yet a further embodiment, the wound dressing, comprises the impregnation thereof with the pharmaceutical composition and optionally antimicrobial or skin/tissue calming agents.

In one embodiment, the present invention provides a method for treating a subject afflicted with a bleeding disorder, comprising administering to the subject a therapeutically effective amount of the pharmaceutical composition described herein. In another embodiment, the subject is afflicted with hemophilia.

In one embodiment, the present invention provides a method of preventing anticoagulation in a subject afflicted thereby, comprising administering a therapeutically effective amount of the peptide or the composition described herein. In a specific embodiment, the method comprises the administering of a therapeutically effective amount of the pharmaceutical composition described herein, prior to medical procedures. In another specific embodiment, a method of preventing anticoagulation in a subject comprises the administration of a therapeutically effective amount of the peptide or the pharmaceutical composition prior to surgery.

In a still further embodiment, the present invention provides a method of promoting wound healing by administering a therapeutically effective amount of the pharmaceutical composition described herein, such as part of a wound dressing.

In another embodiment, the method comprises applying a therapeutically effective amount of the pharmaceutical composition to the subject topically. In another embodiment, the method comprises applying a therapeutically effective amount of the pharmaceutical composition to the subject intravenously. In another embodiment, the method comprises applying a therapeutically effective amount of the pharmaceutical composition to the subject in a subcutaneous injection.

A "therapeutically effective amount" depends on the severity and course of the disease or condition, previous therapy, the patient's health status, weight, and response to the drugs, and the judgment of the treating physician. Therapeutically effective amounts are optionally determined by methods including, but not limited to, a dose escalation clinical trial. Therapeutically effective amounts include the administration of the pharmaceutical composition described herein for prophylactic purposes.

The compositions described herein may be used to treat a deficiency of a coagulation factor. In one embodiment, the bleeding disorder may be hemophilia. Symptoms of such bleeding disorders include, for example, severe epistaxis, oral mucosal bleeding, hemarthrosis, hematoma, persistent hematuria, gastrointestinal bleeding, retroperitoneal bleeding, tongue/retropharyngeal bleeding, intracranial bleeding, and trauma-associated bleeding.

The peptides and compositions of the present invention may be used for prophylactic applications. In some embodiments, the peptide or pharmaceutical composition of the present invention may be administered to a subject susceptible to or otherwise at risk of a disease state or injury, to enhance the subject's own coagulative capability. Such an amount may be defined to be a "prophylactically effective amount". Administration of the procoagulant peptide or composition for prophylaxis comprises situations where a patient suffering from hemophilia, other blood coagulation disorders or is about to undergo medical treatment or surgery, and the peptide is administered between one to four hours prior to surgery. In addition, the peptide is suitable for use as a prophylactic against uncontrolled bleeding, optionally in patients not suffering from hemophilia. Thus, for example, the peptide may be administered to a patient at risk for uncontrolled bleeding prior to surgery.

In another embodiment, the invention relates to a method of treating a subject with a hemostatic disorder comprising administering a therapeutically effective amount of the procoagulant peptide of the invention in combination with at least one other clotting factor or agent that promotes hemostasis. The other clotting factor or agent that promotes hemostasis can be any therapeutic with demonstrated clotting activity. As an example, but not as a limitation, the clotting factor or hemostatic agent can include factor V, factor VII, factor VIII, factor IX, factor X, factor XI, factor XII, factor XIII, prothrombin, fibrinogen, von Willebrand factor or recombinant soluble tissue factor (rsTF) or activated forms of any of the preceding. The clotting factor of hemostatic agent can also include anti-fibrinolytic drugs, e.g., epsilon-amino-caproic acid, tranexamic acid.

As demonstrated herein, the peptide of the invention causes angiogenesis when administered in an effective angiogenesis promoting amount. Accordingly, in some embodiments, the invention provides a method for promoting angiogenesis in a subject in need thereof, the method comprising administering the subject with a therapeutically effective amount of the pharmaceutical composition of the invention.

Examples of such conditions amenable to treatment by promoting angiogenesis are provided herein and can include occlusive vascular disease, coronary disease, erectile dysfunction, myocardial infarction, ischemia, stroke, peripheral artery vascular disorders, and wounds.

The peptide of the invention may be administered directly to the site requiring promotion of angiogenesis, e.g., a diseased area or a wound or burn site. This means that the route of administration such as injections and topical administration are particularly suitable. For example, a surgeon can make an incision to expose a desired area and the peptide is applied directly to the desired locus using a spatula, syringe, or by sprinkling. These techniques can be applied to cartilaginous areas, to ligamentous areas, organs, or any other internal locations in a patient where angiogenesis is desired. In addition, in the case of a surface wound, the peptide can be applied directly to the locus of the wound site and optionally covered. It is thus also contemplated that the peptide can be applied in the form of a dressing to the wound site. The peptide can be applied directly, without a vehicle or can be applied in the form of, e.g., a powder, gel, ointment, paste, fluid or lotion. Methods of incorporating substances into the aforementioned dosage forms are well known in the art and are described, e.g., in Remington's Pharmaceutical Sciences, 17th ed., Mack Publishing Company, 1985, incorporated herein by reference. One skilled in the art would recognize that various carriers, diluents, adjuvants, and so forth may be used in combination with the peptide in order to enhance their delivery. All such combinations and variations are embraced by the present method of promoting angiogenesis.

In another embodiment, the invention provides a diagnostic method for the detection and/or monitoring of a coagulation-related pathologic disorder in a mammalian subject. In another embodiment, the invention provides a method for determining hemostatic activity in a biological sample of a mammalian subject. In some embodiments, the method of the invention comprises the step of: (a) contacting the peptide of the invention and with a biological sample; and (b) determining the coagulation activity within the sample. In some embodiments, the method further comprises comparing the value of coagulation activity of the biological sample to a predetermined control value or to a value of coagulation activity of a control sample. In some embodiments, a higher or lower level of coagulation activity in the biological sample as compared to the control sample or the predetermined control value is indicative of a coagulation-related pathologic disorder in the subject.

In another embodiment, the invention provides a method for determining coagulant activity of a candidate molecule in a biological sample of a mammalian subject. In some embodiments, the method of the invention comprises the step of: (a) contacting the peptide of the invention and a candidate compound with a biological sample; and (b) determining the effect of the candidate compound to mediate the coagulation activity within the sample. In some embodiments, the method further comprises comparing the value of coagulation activity of the biological sample to a predetermined control value or to a value of coagulation activity of a control sample. In some embodiments, a higher or lower level of coagulation activity in the biological sample as compared to the control sample or the predetermined control value is indicative of a coagulant activity of the candidate molecule.

In another embodiment, the invention provides a diagnostic kit for the detection and/or monitoring of a coagulation-related pathologic condition in a mammalian subject. In some embodiments, the kit comprises the peptide of the invention.

General

As used herein the term "about" refers to ±10%.

The terms "comprises", "comprising", "includes", "including", "having" and their conjugates mean "including but not limited to". The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition. Further, treat, treatment, treating, as used herein, means any of the following: the reduction in severity of a hemostatic disorder; the prophylaxis of one or more symptoms associated with a hemostatic disorder, e.g., a bleeding episode; the reduction in the duration of a disease course of a hemostatic disorder; the amelioration of one or more symptoms associated with a hemostatic disorder; the reduction in duration of a bleeding episode associated with a hemostatic disorder; the provision of beneficial effects to a subject with a hemostatic disorder, without necessarily curing the hemostatic disorder.

As used herein, the terms "preventing" or "prevention" of a disease, disorder, or condition encompasses the delay, prevention, suppression, or inhibition of the onset of a disease, disorder, or condition. As used in accordance with the presently described subject matter, the term "prevention" relates to a process of prophylaxis in which a subject is exposed to the presently described compositions or composition prior to the induction or onset of the disease/disorder process. This could be done where an individual has a genetic pedigree indicating a predisposition toward occurrence of the disease/disorder to be prevented. For example, this might be true of an individual whose ancestors show a predisposition toward certain types of, for example, inflammatory disorders. The term "suppression" is used to describe a condition wherein the disease/disorder process has already begun but obvious symptoms of the condition have yet to be realized. Thus, the cells of an individual may have the disease/disorder, but no outside signs of the disease/disorder have yet been clinically recognized. In either case, the term prophylaxis can be applied to encompass both prevention and suppression. Conversely, the term "treatment" refers to the clinical application of active agents to combat an already existing condition whose clinical presentation has already been realized in a patient.

As used herein, "treating" comprises ameliorating and/or preventing.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments unless the embodiment is inoperative without those elements.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Various embodiments and aspects of the present invention as delineated hereinabove and as claimed in the claims section below find experimental support in the following examples.

EXAMPLES

Generally, the nomenclature used herein and the laboratory procedures utilized in the present invention include chemical, molecular, biochemical, and cell biology techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); "Cell Biology: A Laboratory Handbook", Volumes I-III Cellis, J. E., ed. (1994); The Organic Chemistry of Biological Pathways by John McMurry and Tadhg Begley (Roberts and Company, 2005); Organic Chemistry of Enzyme-Catalyzed Reactions by Richard Silverman (Academic Press, 2002); Organic Chemistry (6th Edition) by Leroy "Skip" G Wade; Organic Chemistry by T. W. Graham Solomons and, Craig Fryhle.

The conjugates, materials, compositions, and methods described herein are intended to be representative examples of the invention, and it will be understood that the scope of the invention is not limited by the scope of the examples. Those skilled in the art will recognize that the invention may be practiced with variations on the disclosed peptides, materials, compositions and methods, and such variations are regarded as within the ambit of the invention.

The foregoing examples of the related art and limitations related therewith are intended to be illustrative and not exclusive. Other limitations of the related art will become apparent to those of skill in the art upon a reading of the specification and a study of the figures.

Example 1

Coagulation Effect of Modified Peptides of the Invention

The inventors have recently identified the putative procoagulant domain in heparanase that is involved in coagulation system-activation. In order to enhance the coagulation activity of the peptide comprising the procoagulant domain (denoted "peptide 16"), the inventors have generated 3 modified peptides: (i) Peptide 16C (acetyl-GSKRRKLRVYLHCT; SEQ ID NO: 5); (ii) Peptide 16A (GSKRRKLRVYLHCT-amid; SEQ ID NO: 6); and (iii) Peptide 16AC (acetyl-GSKRRKLRVYLHCT-amid; SEQ ID NO: 7).

Peptides 16, 16C, 16A and 16AC were studied in an assay of purified proteins that included lipidated TF (0.004 μM), factor VIIa (0.04 μM), factor X (1.4 μM) and assay buffer. Factor X activated form (Xa) level was studied using a chromogenic substrate (1 mM). The peptides at a dose of 5 μg/ml and 10 μg/ml (3.75 UM and 7.5 M, respectively) significantly increased activation of factor X compared to control (FIG. 1A), thus increasing activation of the coagulation system. Bovine factor Xa diluted in the assay buffer was used to generate a standard curve. Without addition of TF (two right columns), no factor Xa was generated. These results represent a mean of triplicate and range. *$p<0.01$, $p<0.001$, *$p<0.0001$.

Figure 1B:
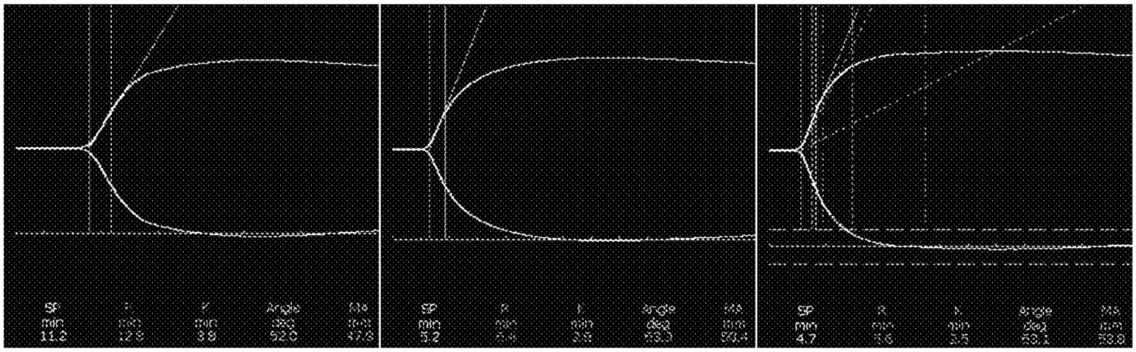
Figure 1C:
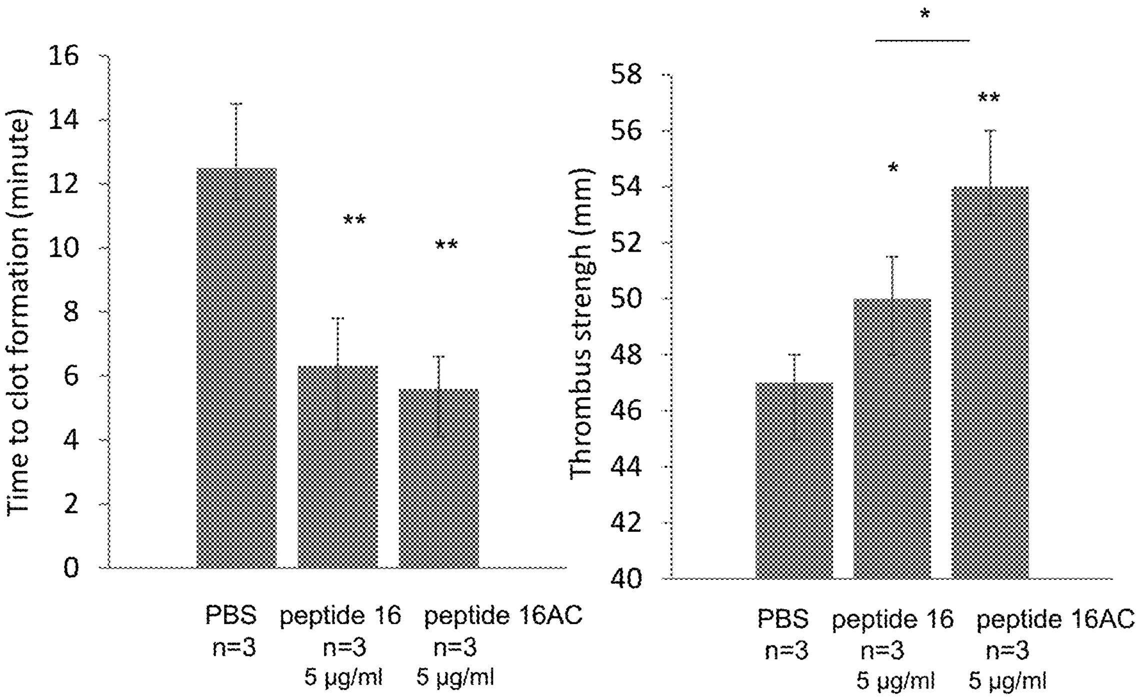

A citrated pooled normal human blood sample (n=3) was left for 4 hours at room temperature in order to expose TF in bloods cells. Following this period, the peptides 16 and 16AC were added (5 μg/ml) along with calcium. The peptides significantly reduced the time to clot formation (R) and increased thrombus strength, as indicated by a greater maximal amplitude (MA). Representative images are shown (FIG. 1B). The study from B section was repeated 3 times with different pooled blood. These results represent a mean of triplicate and range. *$p<0.01$, $p<0.001$. The modified peptide 16AC demonstrated a significant better effect to increase clot formation compared to peptide 16 (FIG. 1**C).

As shown in Example 1, the modified peptide, specifically peptide 16 being C-terminally amidated, and particularly C-terminally amidated and N-terminally acetylated (16AC), surprisingly demonstrated an elevated improvement in clot formation.

Example 2

Reduced Bleeding Using Procoagulant Modified Peptides

Figure 2A:
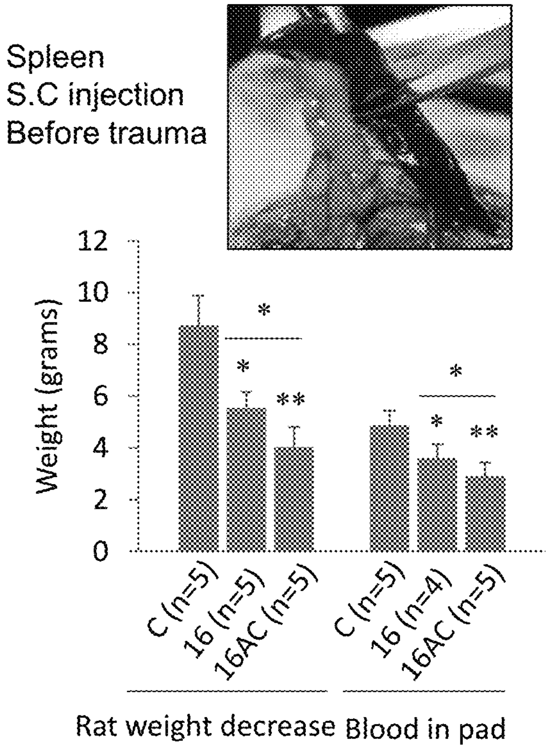
FIGS. 2A-2I include vertical bar graphs showing the effect of modified heparanase procoagulant peptides of the invention using different rat bleeding models. Two rat models of uncontrolled hemorrhage were applied. The models include spleen transection (2A) and liver laceration (2B). Blood loss was recorded every 2 minutes for the first 10 minutes after injury and at 5-minutes intervals thereafter for a total of 30 minutes. Shed blood were collected by placing reweighed gauze below the organ targeted for injury. The gauze was changed and weighed at the blood-loss intervals. Peptides 16 and 16AC were injected subcutaneously (150 μg/kg) half an hour before surgery (2A-2B) or intravenously (I.V.) in the saphenous vein (150 μg/kg) 2 minutes following the trauma (2C, 2D, 2H, and 2I). The third route of administration was topical application (150 μg/kg) on the incision site (2E-2F). The peptides were dissolved in phosphate-buffered saline (PBS) and added at a rate of a drop every 5 seconds. Control group ('C') was administered (either subcutaneously, intravenously, or topically) with the vehicle phosphate buffered saline (PBS). A significant reduction in bleeding (2A-2F) and in bleeding time (2G) was observed when the peptides were applied. The difference in the rat weight before and at the end of the procedure and the pads with blood weight were significantly decreased in the study group compared to control. The modified peptide 16AC demonstrated a significant better effect to reduce the bleeding compared to peptide 16. n—number of mice. Mann-Whitney U test was used. Results represent mean±SD. *p<0.01, p<0.001. In addition to Peptide 16 and Peptide 16AC, Peptide 16C, and Peptide 16A were also analyzed and compared in (2H and 2**I).
Figure 2B:
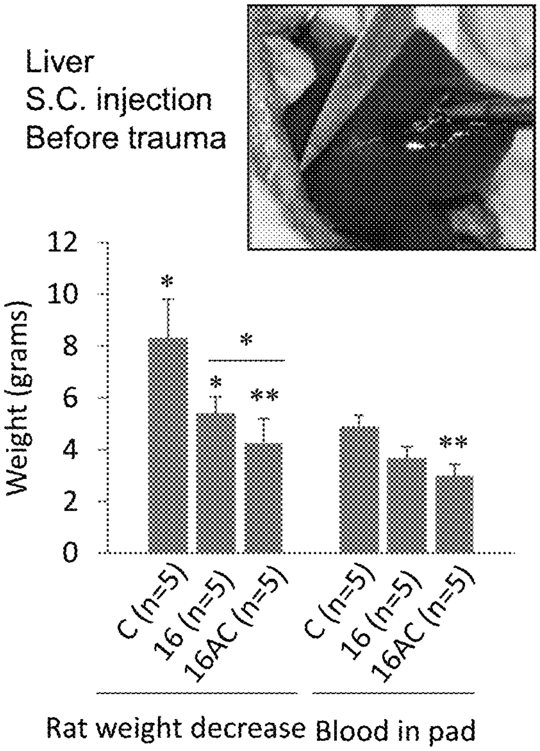
Figure 2C:
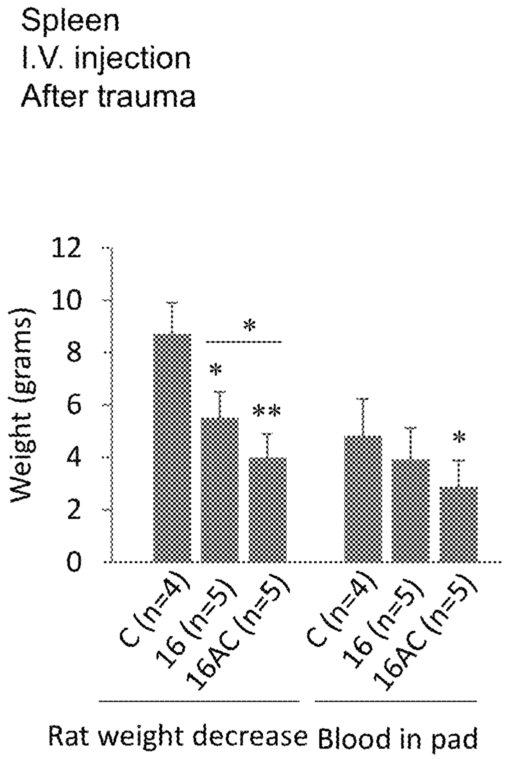
Figure 2D:
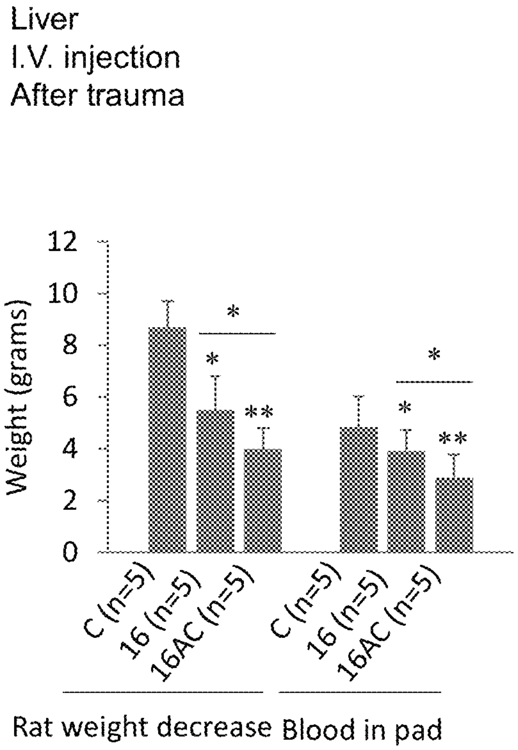
Figure 2E:
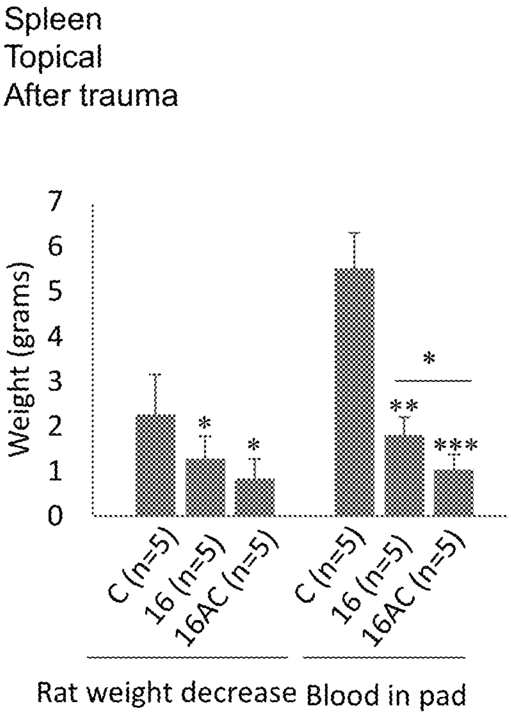
Figure 2F:
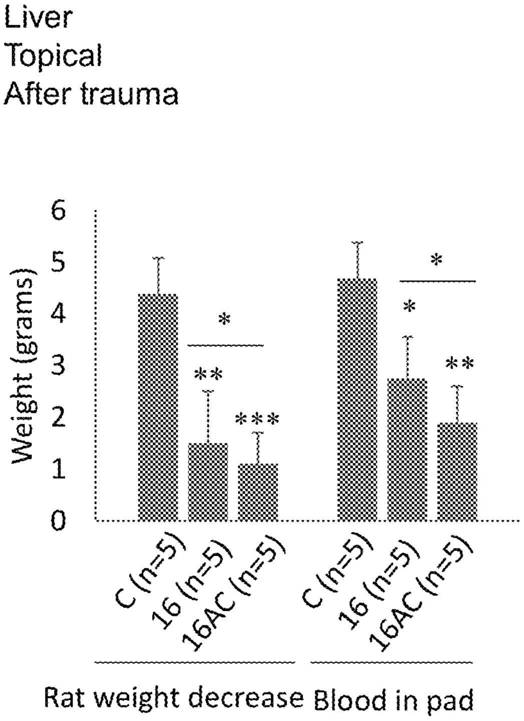
Figure 2G:
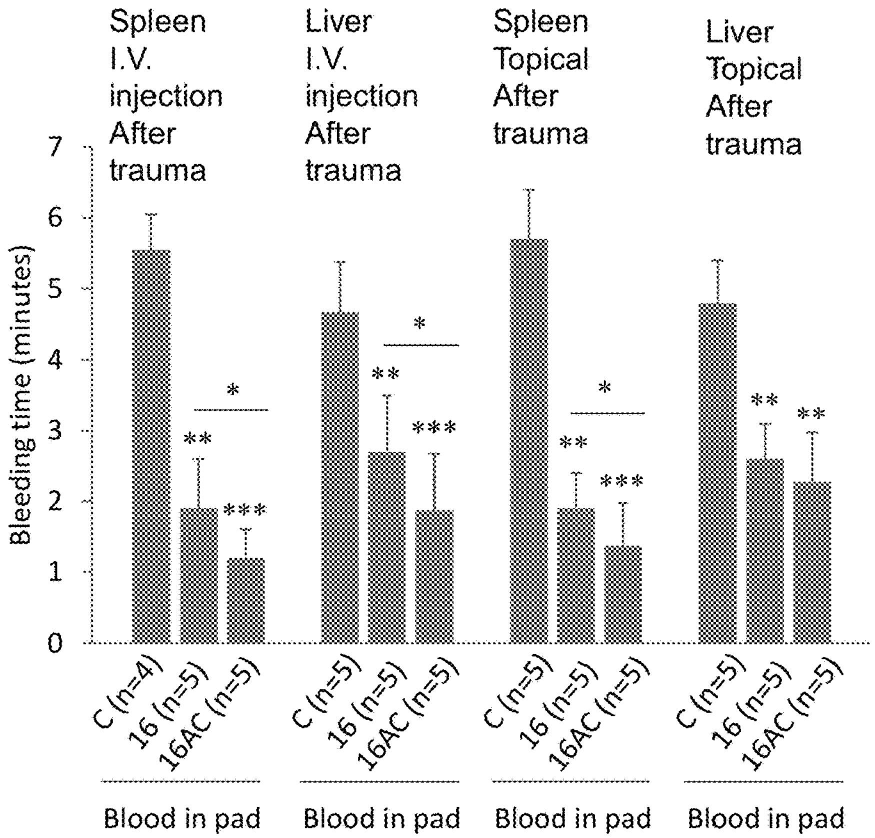

Two rat models of uncontrolled hemorrhage were applied as previously described (Morgan et al., 2015; JAMA Surg.). The models included spleen transection (FIG. 2A) and liver laceration (FIG. 2B). Briefly, blood loss was recorded every 2 minutes for the first 10 minutes after injury and at 5-minute intervals thereafter for a total of 30 minutes. Shed blood were collected by placing reweighed gauze below the organ targeted for injury. The gauze was changed and weighed at the blood-loss intervals. Peptides 16 and 16AC were injected subcutaneous (150 μg/kg) half an hour before surgery (FIGS. 2A-2B) or intra-venous (I.V.) in the saphenous vein (150 μg/kg) 2 minutes following the trauma (FIGS. 2C-2D). The third route of administration was topical application (150 μg/kg) on the incision site (FIGS. 2E-2F). The peptides, dissolved in phosphate-buffered saline (PBS), were added at a rate of a drop every 5 seconds. Control (C) group was injected or topical applied with the vehicle phosphate buffered saline (PBS). A significant reduction in bleeding (FIGS. 2A-2F) and in bleeding time (FIG. 2G) was observed when the peptides were applied. The difference in the rat weight before and at the end of the procedure and the pads with blood weight were significantly decreased in the study group compared to control.

Figure 2H:
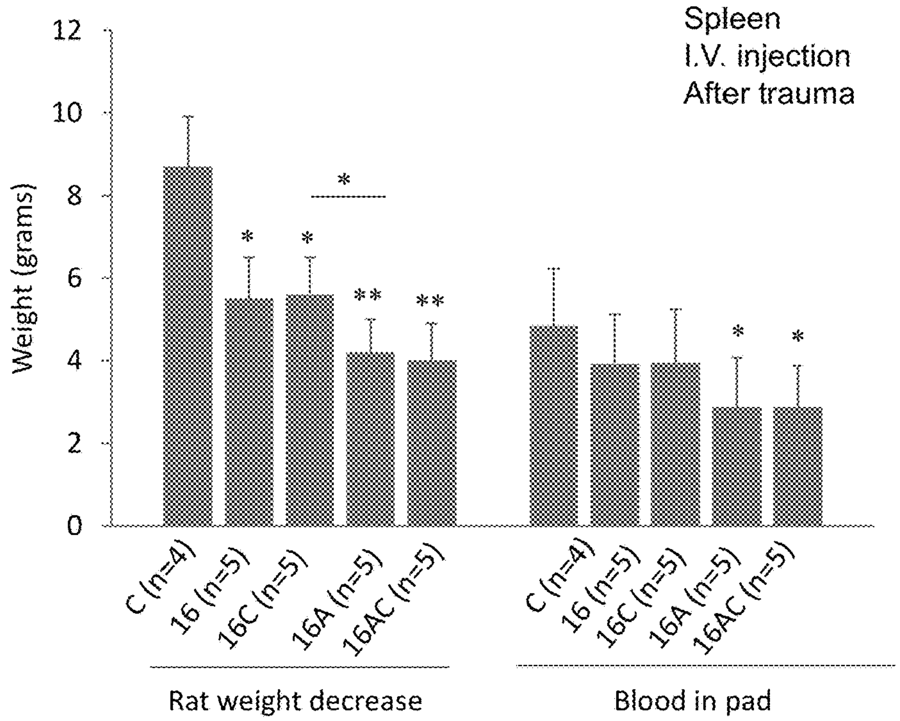
Figure 2I:
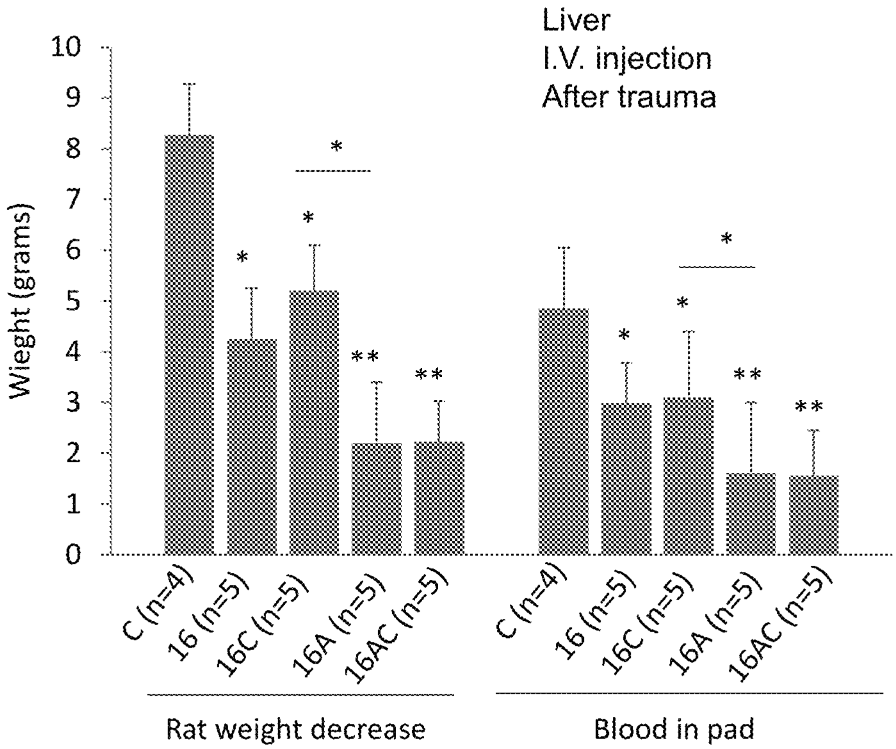

The modified peptide 16AC demonstrated a significantly better effect in reducing the bleeding compared to peptide 16. Effect of peptide 16C was similar to that of 16, and effect of 16A was similar to that of 16AC (FIGS. 2H-2I), both of which were superior to peptide 16 and peptide 16C. This result implies that the addition of positive charge to the peptide by the amide group further increased the therapeutic efficacy of the peptide.

Example 3

Reduced Bleeding Using Procoagulant Modified Peptides

Figure 3A:
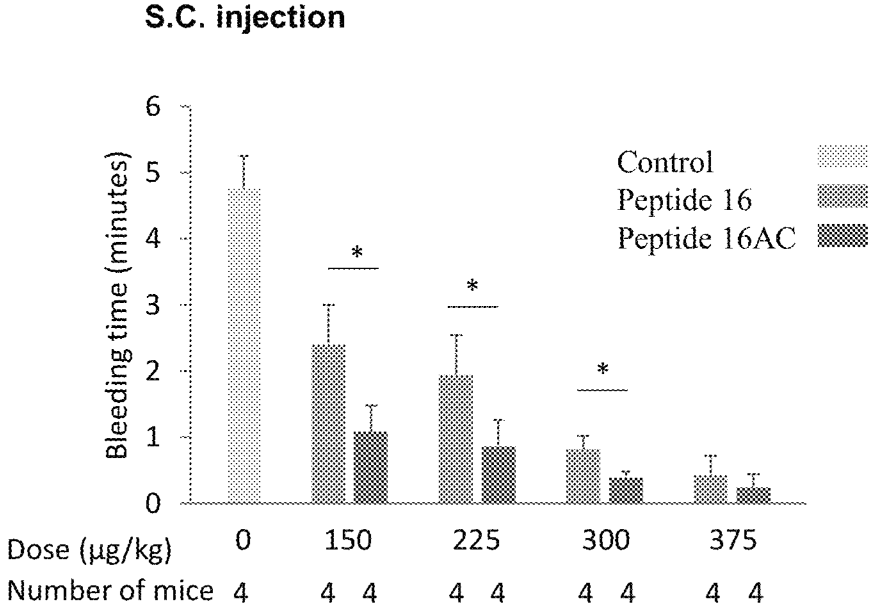
FIGS. 3A-3D include vertical bar graphs showing that modified heparanase procoagulant peptides of the invention decrease bleeding in hemophilic mice. Hemophilic mice (VIII-KO mice; C57BL/6 background, strain name B6;129S4-F8tm1Kaz/J) were studied. (3A) Peptides 16 or 16AC were injected subcutaneously at the flank in doses 150, 225, 300, 375 μg/kg. A mouse-tail bleeding time model was performed. The peptides were dissolved in phosphate-buffered saline (PBS). Control (0) group was injected with the vehicle phosphate buffered saline (PBS). (3D) is identical to (3A) with the exception that peptide 16 C (comprising a C-terminal amid group) and peptide 16A (comprising an N-terminal acetyl group) were also administered in the disclosed doses. In a similar study, the peptides were topically applied on the tail immediately following the incision of the tail at a rate of a drop every 5 seconds (3B). Comparable results were obtained when peptides were dissolved in white soft paraffin (Rekah Pharma Industry, Israel) and applied in a very thin layer (0.25 μm) on the flanked, following hair removal, 1 hour prior to tail incision (3C). A significant decrease in bleeding time was observed in the hemophilic mice in a dose dependent manner. The modified peptide 16AC demonstrated a significant better effect to reduce the bleeding time compared to peptide 16. Mann-Whitney U test was used. Results represent mean±SD. *p<0.05.
Figure 3B:
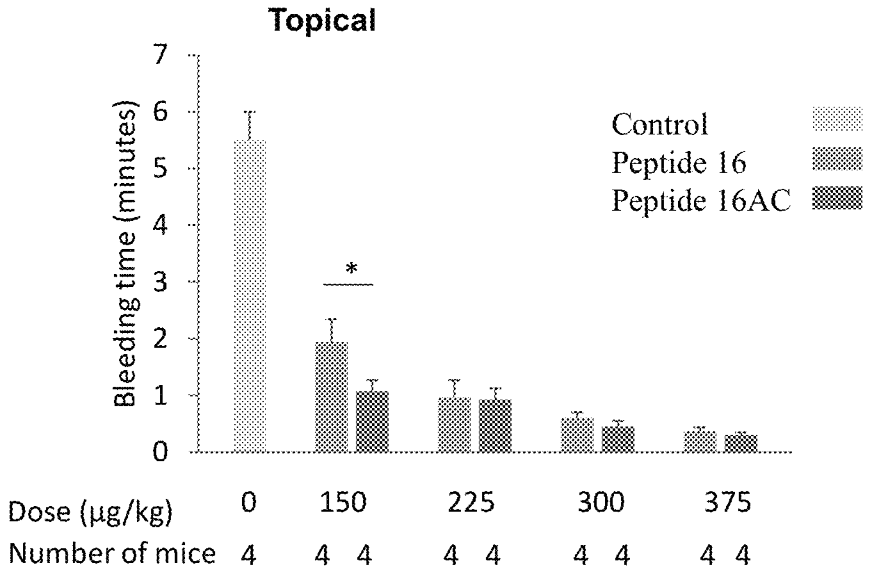
Figure 3C:
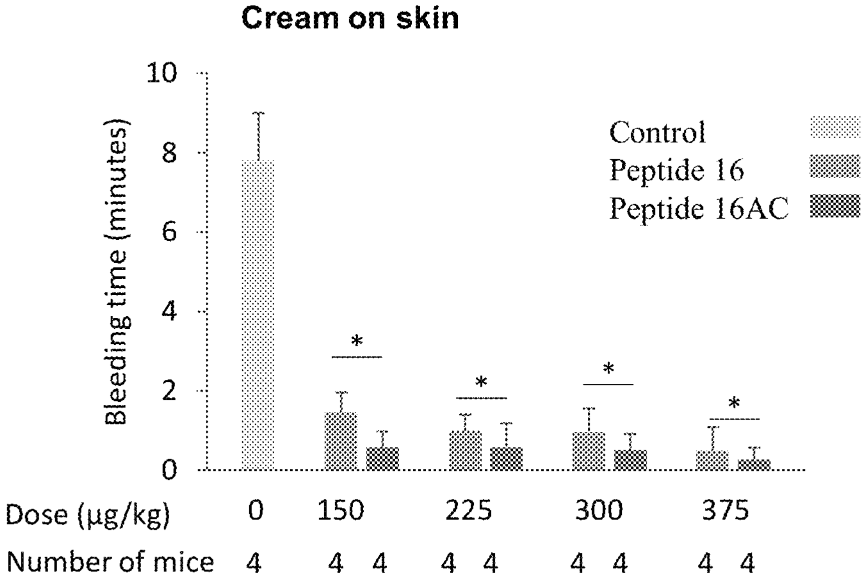
Figure 3D:
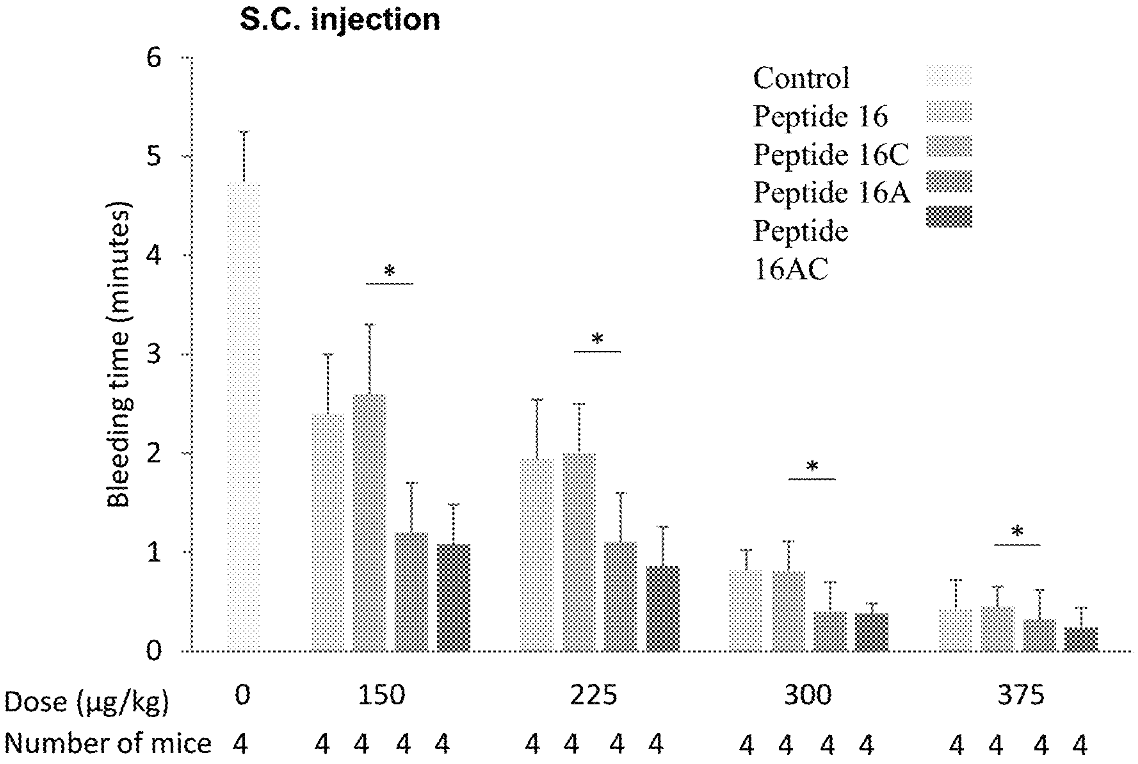

Hemophilic mice (VIII-KO mice; C57BL/6 background, strain name B6;129S4-F8tm1Kaz/J) were studied. Peptides 16 or 16AC were injected sub-cutis at the flank in doses 150, 225, 300, 375 μg/kg. A mouse-tail bleeding time model was performed. The peptides were dissolved in phosphate-buffered saline (PBS). Control (0) group was injected with the vehicle phosphate buffered saline (PBS) (FIGS. 3A and 3D). In a similar study, the peptides were topically applied on the tail immediately following the incision of the tail at a rate of a drop every 5 seconds (FIG. 3B). Comparable results were obtained when peptides were dissolved in white soft paraffin (Rekah Pharma Industry, Israel) and applied in a very thin layer (0.25 μm) on the flanked, following hair removal, 1 hour prior to tail incision (FIG. 3C). A significant decrease in bleeding time was observed in the hemophilic mice in a dose dependent manner. The C-terminal amidated peptide 16 demonstrated a significant better effect to reduce the bleeding time compared to peptide 16 and peptide 16C (FIG. 3D). In particular, C-terminally amidated and N-terminally acetylated peptide 16 (i.e., 16AC), demonstrated an improved bleeding reduction.

Example 4

Wound Healing Using Procoagulant Modified Peptides

Figure 4A:
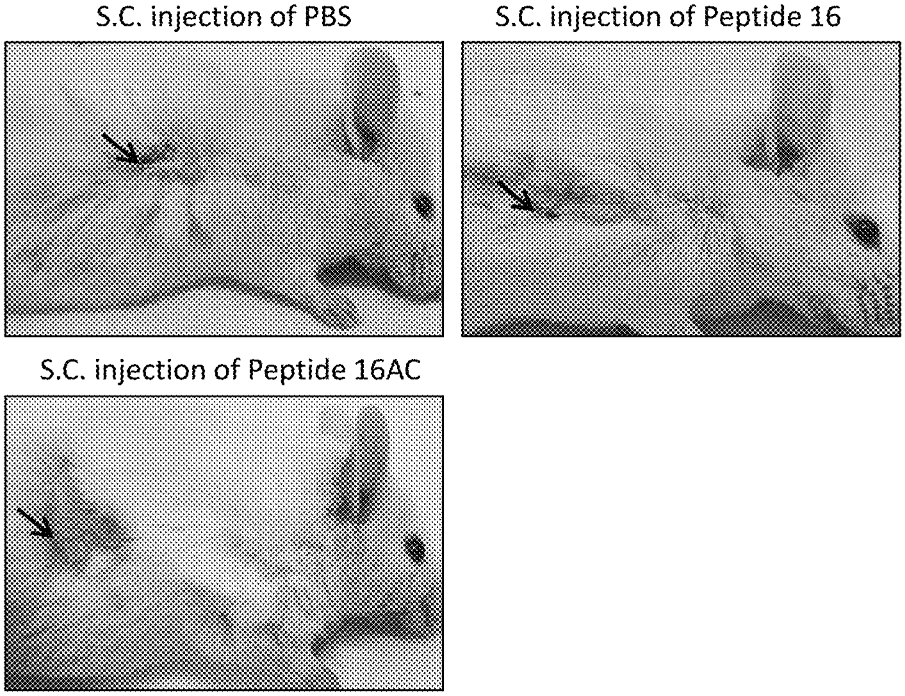
FIGS. 4A-4E include images, micrographs, and graphs showing that that modified heparanase procoagulant peptides of the invention enhance wound healing. (4A) Full thickness incision of 10 mm was made in the back skin of ICR (normal, no genetic background) mice. On alternate days, for one week after surgery, peptide 16 or peptide 16AC was injected subcutaneously (S.C.) opposite to the wound at the indicated dose. Control group was injected the vehicle (PBS). Modified peptide 16AC demonstrated significantly better effect on wound size healing (4A; black arrows, and 4B). Similar results were observed when the peptides were topically applied as a cream preparation (4C). n—number of mice. Mann-Whitney U test was used. Results represent mean±SD, p<0.001, *p<0.0001. (4D) At the end of the experiment the mice were sacrificed and the skin tissue from the wound site excised, and histologically analyzed using hematoxylin and eosin (H&E) staining. Representative images are shown. A significant increase of capillaries (4D; black arrows) was observed in the skin tissue of the treatment groups, compared to control (4E). The number of capillaries presented reflects the median and range of five different fields. Mann-Whitney U test was used. Results represent mean±SD, *p<0.01, **p<0.001.
Figure 4B:
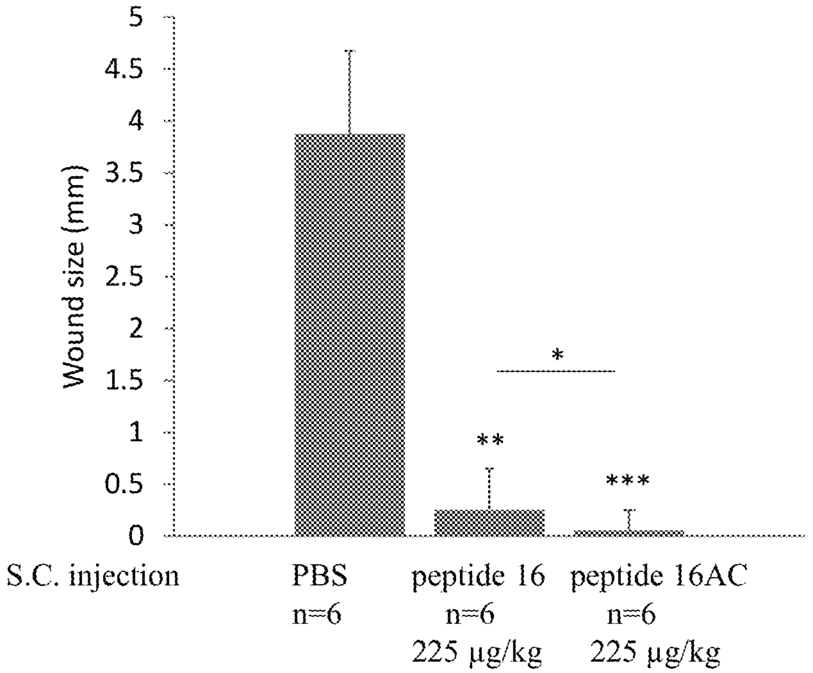
Figure 4C:
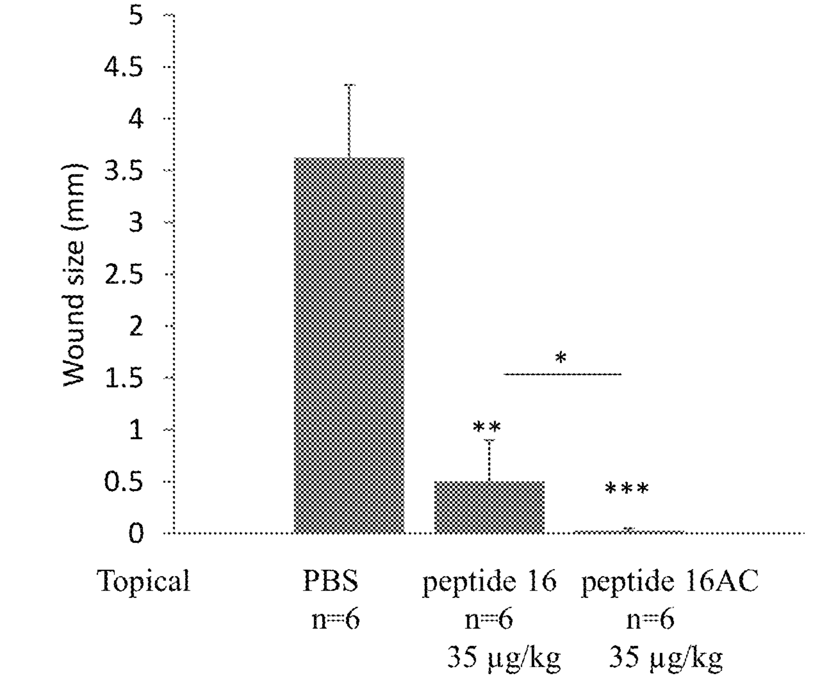
Figure 4D:
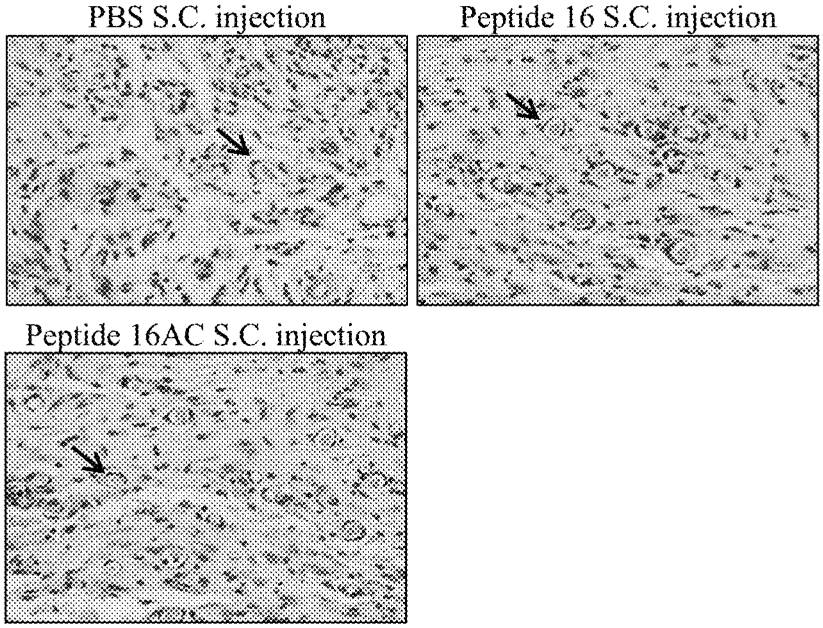
Figure 4E:
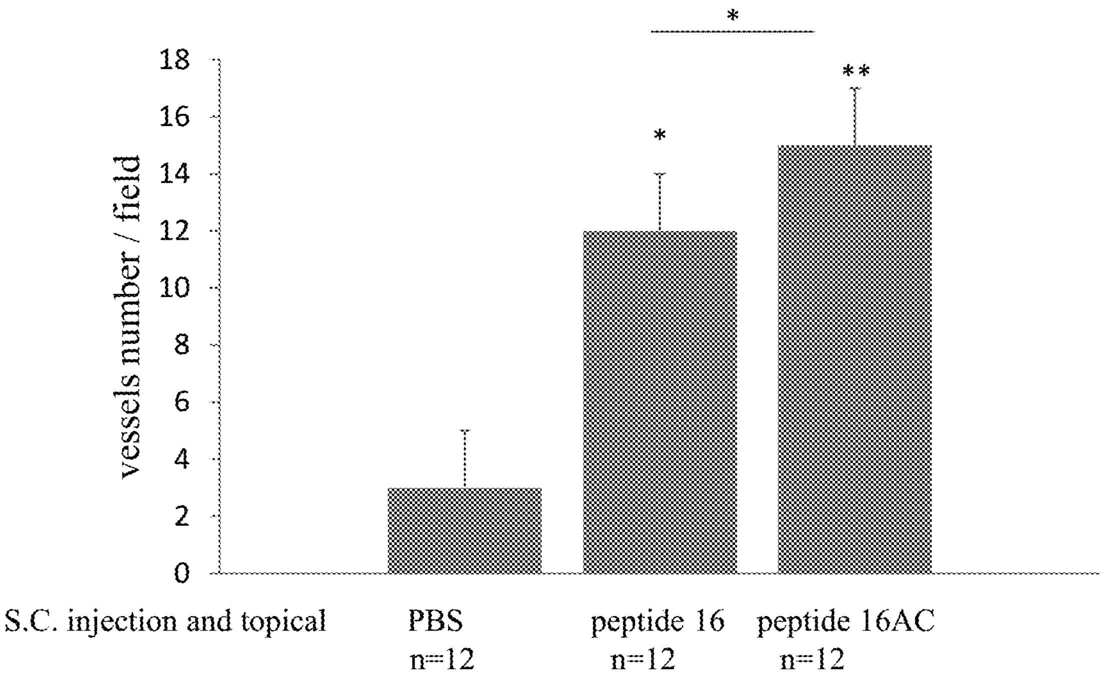

Full thickness incision of 10 mm was made in the back skin of ICR (normal, no genetic background) mice. On alternate days, for one week after surgery, peptide 16 was injected sub-cutaneous (S.C.) opposite to the wound at the indicated dose. Control group was injected the vehicle (PBS). Peptide significantly enhanced wound healing (FIGS. 4A-4B). Similar results were obtained when the peptides were applied topically in a cream preparation (FIG. 4C). At the end of the experiment the mice were sacrificed and the skin tissue from the wound site was analyzed using H&E staining. A significant increase of capillaries was observed in the skin tissue in the treatment groups compared to control (FIGS. 4D-4E).

As seen in Example 4, the modified peptide 16AC demonstrated a significantly better effect on wound size and vessels number compared to peptide 16.

Example 5

Figure 5A:
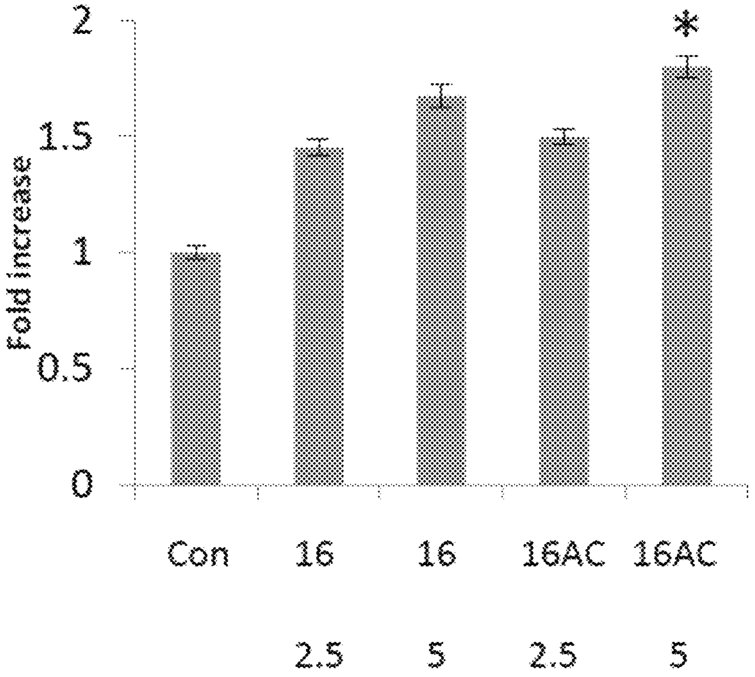
FIGS. 5A-5B include vertical bar graphs showing that heparanase procoagulant peptides induce human umbilical vein endothelial cells (HUVEC) proliferation. (5A) HUVEC cells were seeded in 96 wells plate (5,000 cells/well). Increasing concentration of peptides 16 and 16AC (2.5 μg/ml, and 5 μg/ml) were added to the cells. After 48 hour, using the XTT assay, a significant increase in cell proliferation was observed (*P<0.05). (5B) Similar experiment as described in 5A, but 10 ng/ml of peptide 7 (TFPI-2 derived inhibitory peptide) was added to the cells for 1 hour prior to the addition of peptide 16 (5 μg/ml) or 16AC (5 μg/ml). Peptide 7 significantly inhibited the proliferative effect of any one of peptides 16 and 16AC.
Figure 5B:
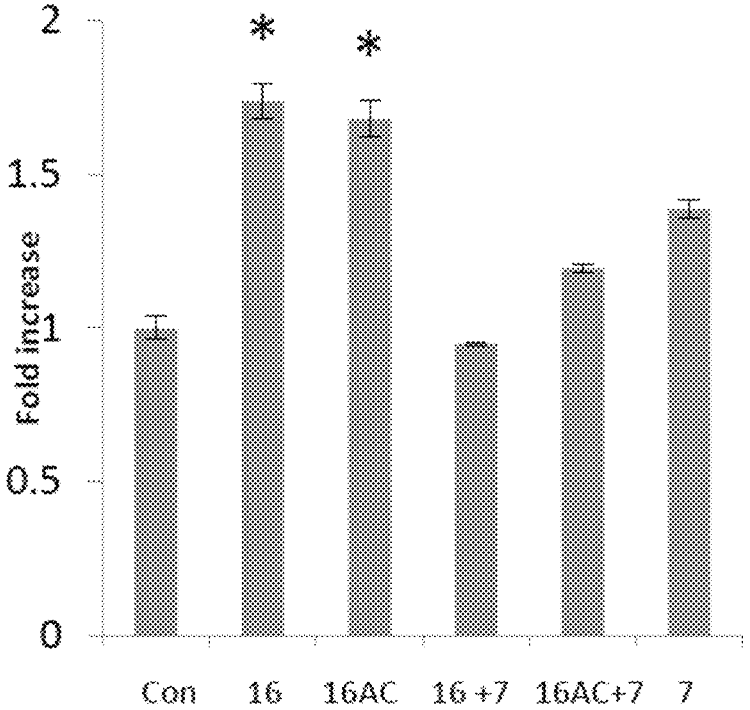
Figure 6:
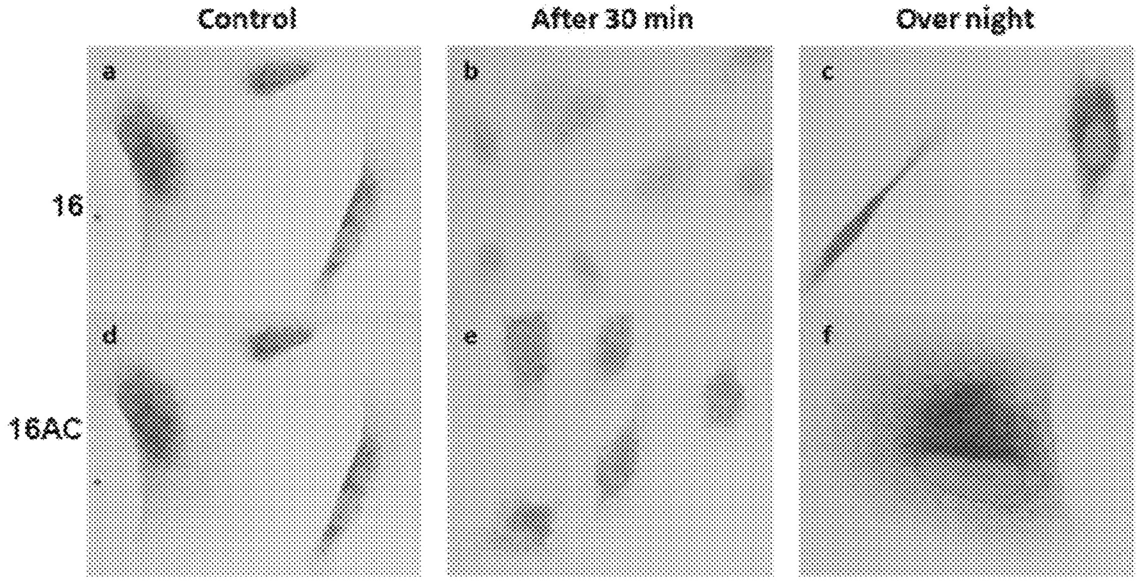
FIGS. 6A-6F include micrographs of immunohistochemistry assays showing that heparanase procoagulant peptides increase the level of heparanase in HUVECs. Ten (10) μg/ml of peptide 16 (6B-6C) or 10 μg/ml of peptide 16AC (6E-6F) was added to HUVEC cells and compared to control cells (6A-6D). After 30 min or overnight incubation at 37° C., the cells were fixed using formaldehyde 4%, permeabilized, blocked and reacted with specific heparanase antibody. A strong staining after overnight incubation in the treated cells compared to the control, indicates heparanase over-expression in treated cells. Images were visualized through ×50 magnitude, with 0.82 MDC objective lens, captured with a Nikon E995 digital camera (Nikon, Tokyo, Japan), and processed with Adobe Photoshop software (Adobe Systems, San Jose, CA, USA).
Figure 7:
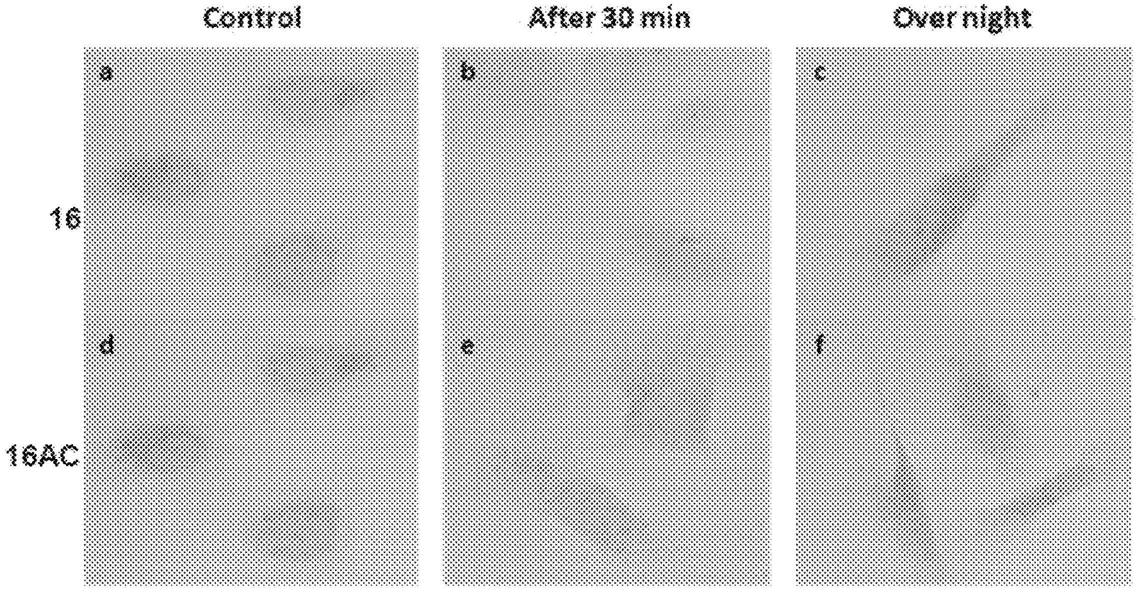
FIGS. 7A-7F include micrographs of immunohistochemistry assays showing that heparanase procoagulant peptides increase the level of TF in HUVECs. Ten (10) μg/ml of peptide 16 (7B-7C) or 10 μg/ml of peptide 16AC (7E-7F) was added to HUVEC cells and compared to control cells (7A-7D). After 30 min or overnight incubation at 37° C., the cells were fixed using formaldehyde 4%, permeabilized, blocked and reacted with specific TF antibody. Images were visualized through ×50 magnitude, with 0.82 MDC objective lens, captured with a Nikon E995 digital camera (Nikon, Tokyo, Japan), and processed with Adobe Photoshop software (Adobe Systems, San Jose, CA, USA).
Figure 8:
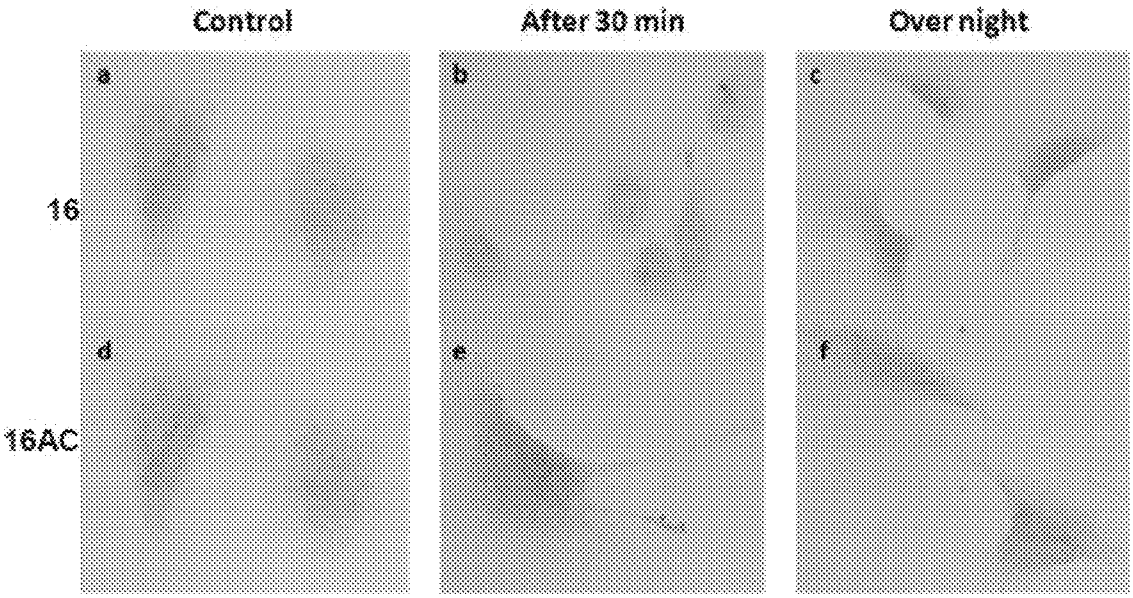
FIGS. 8A-8F include micrographs of immunohistochemistry assays showing that heparanase procoagulant peptides increase the level of TFPI in HUVECs. Ten (10) μg/ml of peptide 16 (8B-8C) or 10 μg/ml of peptide 16AC (8E-8F) was added to HUVEC cells and compared to control cells (8A-8D). After 30 min or overnight incubation at 37° C., the cells were fixed using formaldehyde 4%, permeabilized, blocked and reacted with specific TFPI-1 antibody. Images were visualized through ×50 magnitude, with 0.82 MDC objective lens, captured with a Nikon E995 digital camera (Nikon, Tokyo, Japan), and processed with Adobe Photoshop software (Adobe Systems, San Jose, CA, USA).
Figure 9:
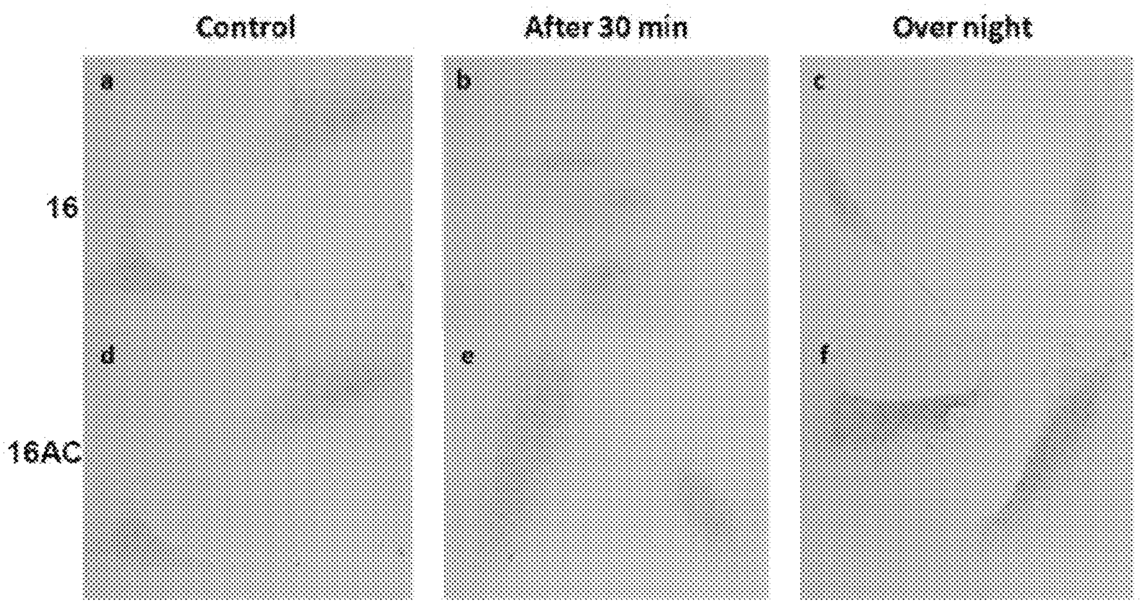
FIGS. 9A-9F include micrographs of immunohistochemistry assays showing that heparanase procoagulant peptides increase the level of TFPI-2 in HUVECs. Ten (10) μg/ml of peptide 16 (9B-9C) or 10 μg/ml of peptide 16AC (9E-9F) was added to HUVEC cells and compared to control cells (9A-9D). After 30 min or overnight incubation at 37° C., the cells were fixed using formaldehyde 4%, permeabilized, blocked and reacted with specific TFPI-2 antibody. Images were visualized through ×50 magnitude, with 0.82 MDC objective lens, captured with a Nikon E995 digital camera (Nikon, Tokyo, Japan), and processed with Adobe Photoshop software (Adobe Systems, San Jose, CA, USA).
Figure 10A:
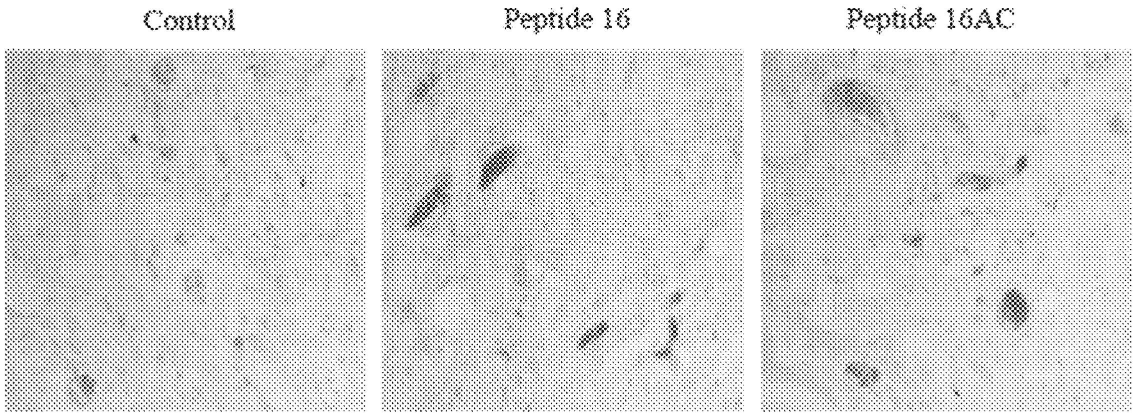
FIGS. 10A-10D include micrographs of immunohistochemistry assays showing that heparanase procoagulant peptides increase the level of heparanase, TF, TFPI and TFPI-2. Full thickness incision was made in the back skin of ICR mice. Each group included 5 mice. From the day of surgery either peptide 16 or 16AC was injected subcutaneous opposite to the wound, every other day for a week. At the end of the experiment the mice were sacrificed and the wound skin section was analyzed by immunostaining. A significant increase in the expression of heparanase (10A), TF (10B), TFPI-1 (10C), and TFPI-2 (10D) were observed in the micro-vessels (endothelial cell and intraluminal). Images were visualized through ×50 magnitude, with 0.82 MDC objective lens, captured with a Nikon E995 digital camera (Nikon, Tokyo, Japan), and processed with Adobe Photoshop software (Adobe Systems, San Jose, CA, USA).
Figure 10B:
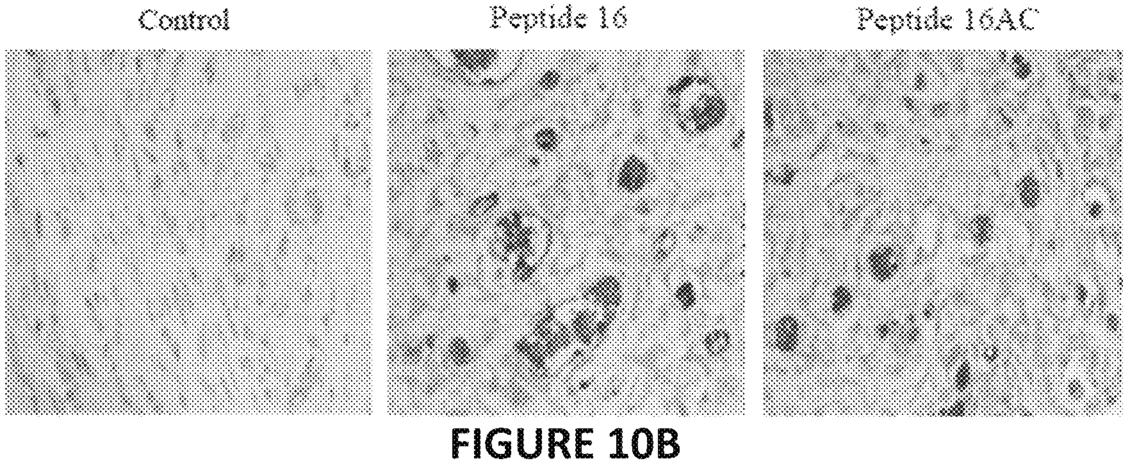
Figure 10C:
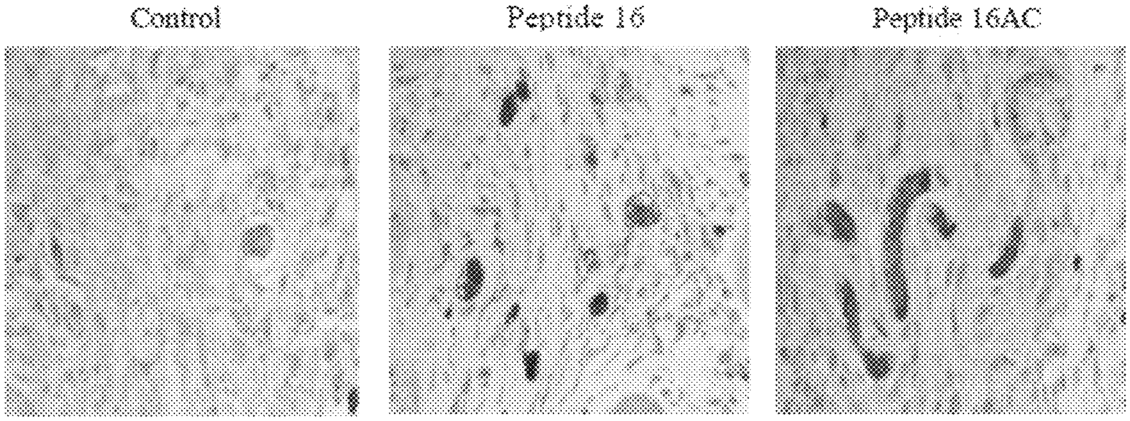
Figure 10D:
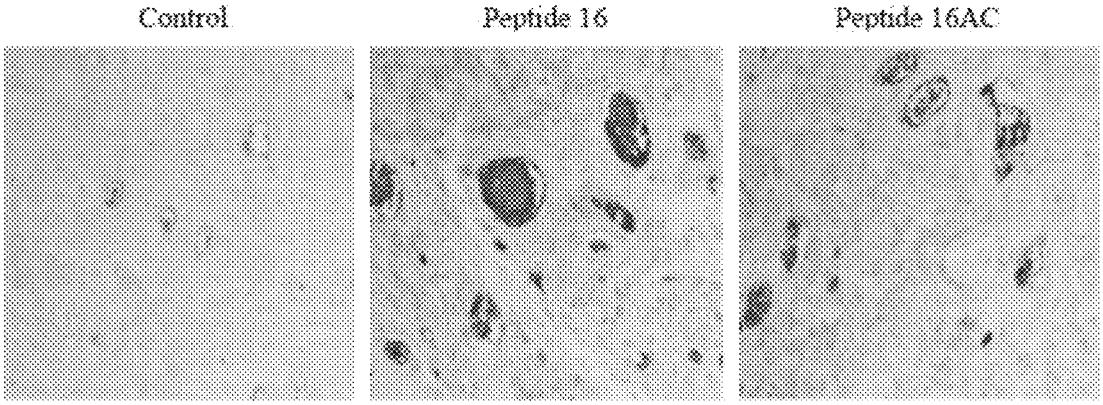

Heparanase Procoagulant Modified Peptides Induce Various Endothelial Cells Activities The inventors showed that heparanase procoagulant peptides of the invention induce human umbilical vein endothelial cells (HUVEC) proliferation. Briefly, HUVEC cells were seeded in 96 wells plate (5,000 cells/well). Increasing concentration of peptides 16 and 16AC (2.5 μg/ml, and 5 μg/ml) were added to the cells. After 48 hour, using the XTT assay, a significant increase in cell proliferation was observed (FIG. 5A). Further, the inventor showed that co-supplementation of peptide 7, a TFPI-2 derived inhibitory peptide, significantly inhibited the proliferative effect of any one of peptides 16 and 16AC (FIG. 5B).

Further, the inventor showed that heparanase procoagulant peptides of the invention increase the level of heparanase, TF, TFPI, and TFPI-2 in HUVECs. Briefly, 10 μg/ml of peptide 16 or 10 μg/ml of peptide 16AC was added to HUVEC cells and compared to control cells (6A-6D). After 30 min or overnight incubation at 37° C., the cells were fixed using formaldehyde 4%, permeabilized, blocked and reacted with specific antibodies targeting heparanase, TF, TFPI-1, and TFPI-2 (FIGS. 6-9, respectively). A strong staining after overnight incubation in the treated cells compared to the control, indicates heparanase, TF, TFPI, and TFPI-2 overexpression in treated cells (FIGS. 6F, 7F, 8F, and 9F, respectively).

Further, the inventor showed that the heparanase procoagulant peptides of the invention, increase the level of heparanase, TF, TFPI and TFPI-2, in vivo. Briefly, full thickness incision was made in the back skin of ICR mice. Each group included 5 mice. From the day of surgery either peptide 16 or 16AC was injected subcutaneous opposite to the wound, every other day for a week. At the end of the experiment the mice were sacrificed and the wound skin section was analyzed by immunostaining. A significant increase in the expression of heparanase, TF, TFPI-1, and TFPI-2 (FIGS. 10A-10D, respectively) were observed in the micro-vessels (endothelial cell and intraluminal) in vivo.

Other, endothelial cell related activity in the context of the current invention, related to cell migration. Thus, the inventor sought to further examine HUVEC cells migration in the presence of the modified peptide 16AC.

Figure 11:
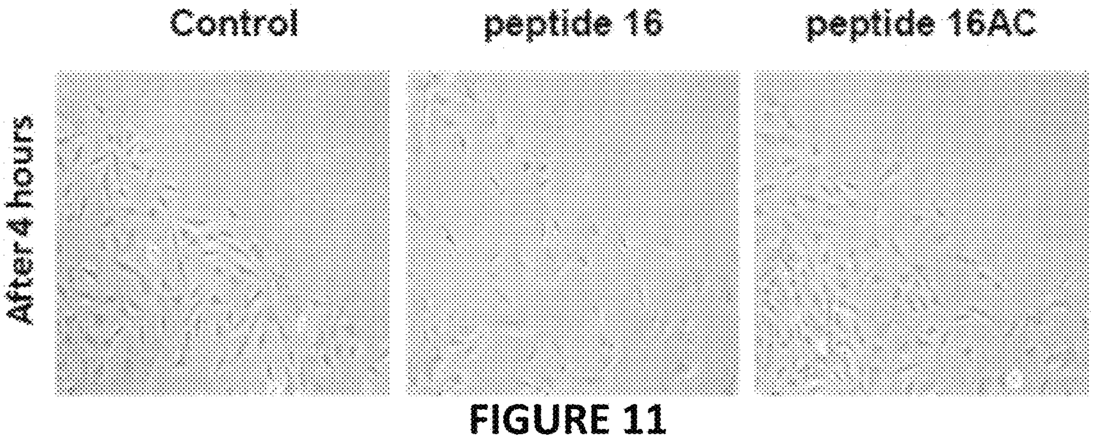
FIG. 11 includes micrographs showing that procoagulant peptides increase endothelial cells migration. HUVEC cells were seeded in 35 mm dishes. At confluence of 90%, artificial gap was created using 1,000-μl standard pipette tip. Plate was washed twice with PBS to remove cell debris and incubated with either peptide 16 or 16AC (10 μg/ml). Representative photos of the scratched area after 4 hours are presented. Images were visualized through ×50 magnitude, with 0.82 MDC objective lens, captured with a Nikon E995 digital camera (Nikon, Tokyo, Japan), and processed with Adobe Photoshop software (Adobe Systems, San Jose, CA, USA).

Briefly, HUVEC cells were seeded in 35 mm dishes. At confluence of 90%, artificial gap was created using 1,000 μl standard pipette tip. Plate was washed twice with PBS to remove cell debris and incubated with either peptide 16 or 16AC (10 μg/ml). A substantial increase in migrating HUVEC cells was observed in the presence of peptide 16AC, compared to the control and the non-modified peptide 16 (FIG. 11).

Figure 12:
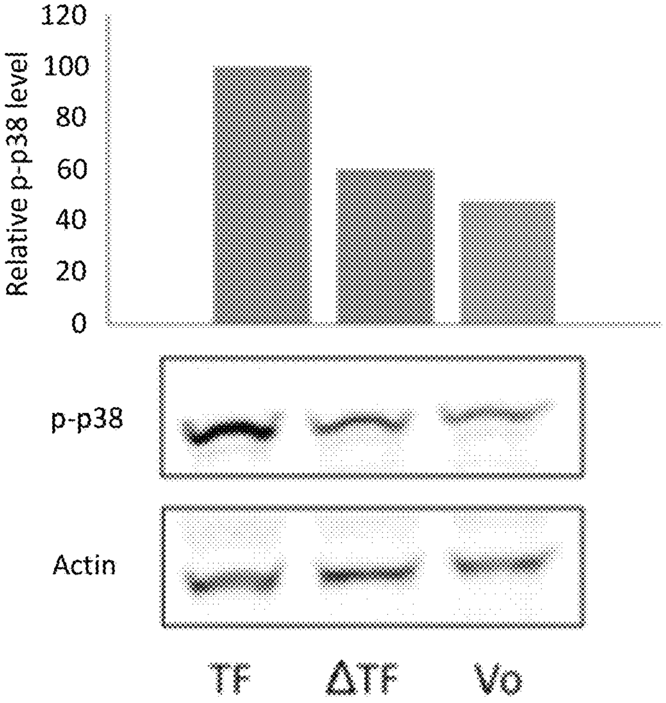
FIG. 12 includes a vertical bar graph and a micrograph of a western blot analysis. Procoagulant peptide 16AC was added for 2 hours to transfected HEK-293 cells with full length TF (TF) or truncated TF devoid of the intracellular part (ΔTF). When the TF was devoid of the intracellular part, an increase in p-p38 intracellular signaling was not observed, thus indicating that TF is a receptor to heparanase at the procoagulant domain. Control—vector only (Vo); transfection with the empty plasmid, with no additional DNA.

Additionally, the inventor explored binding interaction between the procoagulant peptide of the invention and TF. Briefly, the procoagulant peptide 16AC was added for 2 hours to transfected HEK-293 cells with full length TF (TF) or truncated TF devoid of the intracellular part (ATF). When the TF was devoid of the intracellular part, an increase in p-p38 intracellular signaling was not observed, thus indicating that TF is a receptor to heparanase at the procoagulant domain (FIG. 12).

Thus, the inventor concludes that the procoagulant peptide of the invention interacts with TF so as to further intracellularly propagate a signal providing: increased cell proliferation, heparanase release, increased cell migration, upregulation of any one of: heparanase, TF, TFPI, TFPI-2, and any combination thereof, or any combination thereof. Such cell, may be, but is not limited to, an endothelial cell, as exemplified herein. Therefore, the inventor provides that preventing or treating a disease characterized by abnormal or dysfunctional signaling via TF, may find remedy embodied in the modified peptide disclosed herein, and compositions comprising same.

Although the invention has been described in conjunction with specific embodiments thereof, it is evident that many alternatives, modifications, and variations will be apparent to those skilled in the art. Accordingly, it is intended to embrace all such alternatives, modifications and variations that fall within the spirit and broad scope of the appended claims.

What is claimed is:

1. A peptide consisting of the amino acid sequence GSKRRKLRVYLHCT (SEQ ID NO: 2), wherein the N-terminus is acetylated and the C-terminus is amidated.

2. A pharmaceutical composition comprising the peptide of claim 1, and a pharmaceutically acceptable carrier.

3. A wound dressing comprising the peptide of claim 1.

4. A method for treating a subject in need of wound healing, the method comprising administering to said subject a therapeutically effective amount of a pharmaceutical composition comprising a procoagulant peptide consisting of the amino acid sequence GSKRRKLRVYLHCT (SEQ ID NO: 2), wherein the N-terminus is acetylated and the C-terminus is amidated, thereby treating the subject in need of wound healing.

5. A method for treating a subject in need of induction of coagulation, the method comprising administering to said subject a therapeutically effective amount of a pharmaceutical composition comprising a procoagulant peptide consisting of the amino acid sequence GSKRRKLRVYLHCT (SEQ ID NO: 2), wherein the N-terminus is acetylated and the C-terminus is amidated, thereby treating the subject in need of induction of coagulation.

6. The method of claim 5, wherein said subject is afflicted with a wound, hemorrhage, or both.

7. The method of claim 5, wherein said subject is afflicted with a disease or a disorder being selected from the group consisting of: hemostatic disorder, anticoagulation disorder, angiogenesis-related disease, hemophilia, and any combination thereof.

8. The method of claim 5, wherein said administering comprises: subcutaneously administering, intravenously administering, topically administering, or any combination thereof.

* * * * *

SEQUENCE LISTING

```
<160> NUMBER OF SEQ ID NOS: 9

<210> SEQ ID NO 1
<211> LENGTH: 6
<212> TYPE: PRT
<213> ORGANISM: Artificial Sequence
<220> FEATURE:
<223> OTHER INFORMATION: Synthetic

<400> SEQUENCE: 1

Lys Arg Arg Lys Leu Arg
1               5


<210> SEQ ID NO 2
<211> LENGTH: 14
<212> TYPE: PRT
<213> ORGANISM: Artificial Sequence
<220> FEATURE:
<223> OTHER INFORMATION: Synthetic

<400> SEQUENCE: 2

Gly Ser Lys Arg Arg Lys Leu Arg Val Tyr Leu His Cys Thr
1               5                   10


<210> SEQ ID NO 3
<211> LENGTH: 14
<212> TYPE: PRT
<213> ORGANISM: Artificial Sequence
<220> FEATURE:
<223> OTHER INFORMATION: Synthetic

<400> SEQUENCE: 3
```

-continued

Val Gln Gly Ser Lys Arg Arg Lys Leu Arg Val Tyr Leu His
1 5 10

<210> SEQ ID NO 4
<211> LENGTH: 12
<212> TYPE: PRT
<213> ORGANISM: Artificial Sequence
<220> FEATURE:
<223> OTHER INFORMATION: Synthetic

<400> SEQUENCE: 4

Gly Ser Lys Arg Arg Lys Leu Arg Val Tyr Leu His
1 5 10

<210> SEQ ID NO 5
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetyl group

<400> SEQUENCE: 5

Gly Ser Lys Arg Arg Lys Leu Arg Val Tyr Leu His Cys Thr
1 5 10

<210> SEQ ID NO 6
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (14)..(14)
<223> OTHER INFORMATION: Amid group

<400> SEQUENCE: 6

Gly Ser Lys Arg Arg Lys Leu Arg Val Tyr Leu His Cys Thr
1 5 10

<210> SEQ ID NO 7
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetyl group
<220> FEATURE:
<221> NAME/KEY: MISC_FEATURE
<222> LOCATION: (14)..(14)
<223> OTHER INFORMATION: Amid group

<400> SEQUENCE: 7

Gly Ser Lys Arg Arg Lys Leu Arg Val Tyr Leu His Cys Thr
1 5 10

<210> SEQ ID NO 8
<211> LENGTH: 14
<212> TYPE: PRT
<213> ORGANISM: Artificial Sequence
<220> FEATURE:
<223> OTHER INFORMATION: Synthetic -continued

```
<220> FEATURE:
<221> NAME/KEY: MISC_FEATURE
<222> LOCATION: (14)..(14)
<223> OTHER INFORMATION: Amid group

<400> SEQUENCE: 8

Val Gln Gly Ser Lys Arg Arg Lys Leu Arg Val Tyr Leu His
1               5                   10


<210> SEQ ID NO 9
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetyl group
<220> FEATURE:
<221> NAME/KEY: MISC_FEATURE
<222> LOCATION: (14)..(14)
<223> OTHER INFORMATION: Amid group

<400> SEQUENCE: 9

Val Gln Gly Ser Lys Arg Arg Lys Leu Arg Val Tyr Leu His
1               5                   10
```